United States Patent
Thompson-Nauman et al.

(10) Patent No.: US 10,668,270 B2
(45) Date of Patent: Jun. 2, 2020

(54) SUBSTERNAL LEADLESS ELECTRICAL STIMULATION SYSTEM

(71) Applicant: Medtronic, Inc., Minneapolis, MN (US)

(72) Inventors: Amy E. Thompson-Nauman, Ham Lake, MN (US); Melissa G. T. Christie, Andover, MN (US); Paul J. DeGroot, Shoreview, MN (US); Rick D. McVenes, Isanti, MN (US)

(73) Assignee: Medtronic, Inc., Minneapolis, MN (US)

( * ) Notice: Subject to any disclaimer, the term of this patent is extended or adjusted under 35 U.S.C. 154(b) by 525 days.

(21) Appl. No.: 14/261,488

(22) Filed: Apr. 25, 2014

(65) Prior Publication Data

US 2014/0330331 A1 Nov. 6, 2014

Related U.S. Application Data

(60) Provisional application No. 61/820,033, filed on May 6, 2013.

(51) Int. Cl.
*A61N 1/375* (2006.01)
*A61N 1/362* (2006.01)
(Continued)

(52) U.S. Cl.
CPC ............ *A61N 1/05* (2013.01); *A61N 1/0587* (2013.01); *A61N 1/362* (2013.01); *A61N 1/365* (2013.01);
(Continued)

(58) Field of Classification Search
CPC ...... A61N 1/3962; A61N 1/05; A61N 1/3956; A61N 1/0587; A61N 1/3756;
(Continued)

(56) References Cited

U.S. PATENT DOCUMENTS

| | | |
|---|---|---|
| 4,030,509 A | 6/1977 | Heilman et al. |
| 4,146,037 A | 3/1979 | Flynn et al. |

(Continued)

FOREIGN PATENT DOCUMENTS

| | | |
|---|---|---|
| CN | 1859870 A | 11/2006 |
| CN | 102858403 A | 1/2013 |

(Continued)

OTHER PUBLICATIONS (PCT/US2014/036878) PCT Notification of Transmittal of the International Search Report and the Written Opinion of the International Searching Authority, dated Aug. 7, 2014, 8 pages.

(Continued)

*Primary Examiner* — Mark Bockelman
(74) *Attorney, Agent, or Firm* — Shumaker & Sieffert, P.A.

(57) ABSTRACT

Implantable leadless cardiac pacing systems and methods for providing substernal pacing using the leadless cardiac pacing systems are described. In one embodiment, an implantable leadless cardiac pacing system includes a housing, a first electrode on the housing, a second electrode on the housing, and a pulse generator within the housing and electrically coupled to the first electrode and the second electrode. The housing is implanted substantially within an anterior mediastinum of a patient and the pulse generator is configured to deliver pacing pulses to a heart of the patient via a therapy vector formed between the first and second electrodes.

25 Claims, 13 Drawing Sheets

(51) Int. Cl.
  *A61N 1/372* (2006.01)
  *A61N 1/05* (2006.01)
  *A61N 1/365* (2006.01)
(52) U.S. Cl.
  CPC ....... *A61N 1/3756* (2013.01); *A61N 1/37288* (2013.01); *A61N 1/0504* (2013.01)
(58) Field of Classification Search
  CPC .... A61N 1/37288; A61N 1/362; A61N 1/365; A61N 1/0504
  See application file for complete search history.

(56) References Cited

U.S. PATENT DOCUMENTS

| | | | |
|---|---|---|---|
| 4,270,549 A | 6/1981 | Heilman | |
| 4,280,510 A | 7/1981 | O'Neill | |
| 4,291,707 A | 9/1981 | Heilman et al. | |
| 4,437,475 A | 3/1984 | White | |
| 4,512,351 A | 4/1985 | Pohndorf | |
| 4,538,624 A | 9/1985 | Tarjan | |
| 4,708,145 A | 11/1987 | Tacker, Jr. et al. | |
| 4,765,341 A | 8/1988 | Mower et al. | |
| 4,787,389 A | 11/1988 | Tarjan | |
| 4,832,687 A | 5/1989 | Smith, III | |
| 4,865,037 A | 9/1989 | Chin et al. | |
| 5,036,854 A | 8/1991 | Schollmeyer et al. | |
| 5,099,838 A | 3/1992 | Bardy | |
| 5,125,904 A | 6/1992 | Lee | |
| 5,176,135 A | 1/1993 | Fain et al. | |
| 5,193,540 A | 3/1993 | Schulman et al. | |
| 5,203,348 A | 4/1993 | Dahl et al. | |
| 5,255,691 A | 10/1993 | Otten | |
| 5,255,692 A | 10/1993 | Neubauer et al. | |
| 5,273,053 A | 12/1993 | Pohndorf | |
| 5,292,338 A | 3/1994 | Bardy | |
| 5,300,106 A | 4/1994 | Dahl et al. | |
| 5,312,355 A | 5/1994 | Lee | |
| 5,439,484 A | 8/1995 | Mehra | |
| 5,441,504 A | 8/1995 | Pohndorf et al. | |
| 5,456,699 A | 10/1995 | Armstrong | |
| 5,476,493 A | 12/1995 | Muff | |
| 5,509,924 A | 4/1996 | Paspa et al. | |
| 5,534,018 A | 7/1996 | Wahlstrand et al. | |
| 5,613,953 A | 3/1997 | Pohndorf | |
| 5,690,648 A | 11/1997 | Fogarty et al. | |
| 5,721,597 A | 2/1998 | Kakinuma et al. | |
| 5,800,465 A * | 9/1998 | Thompson | A61N 1/368 607/122 |
| 5,944,732 A | 8/1999 | Raulerson et al. | |
| 5,951,518 A | 9/1999 | Licata et al. | |
| 6,032,079 A | 2/2000 | KenKnight et al. | |
| 6,059,750 A * | 5/2000 | Fogarty | A61M 1/1068 601/153 |
| 6,104,957 A | 8/2000 | Alo et al. | |
| 6,120,431 A * | 9/2000 | Magovern | A61M 1/1068 600/17 |
| 6,122,552 A | 9/2000 | Tockman et al. | |
| 6,159,198 A | 12/2000 | Gardeski et al. | |
| 6,228,052 B1 | 5/2001 | Pohndorf | |
| 6,324,414 B1 | 11/2001 | Gibbons et al. | |
| 6,415,187 B1 | 7/2002 | Kuzma et al. | |
| 6,445,954 B1 | 9/2002 | Olive et al. | |
| 6,544,247 B1 | 4/2003 | Gardeski et al. | |
| 6,721,597 B1 | 4/2004 | Bardy et al. | |
| 6,730,083 B2 | 5/2004 | Freigang et al. | |
| 6,733,500 B2 | 5/2004 | Kelley et al. | |
| 6,749,574 B2 | 6/2004 | O'Keefe | |
| 6,770,070 B1 | 8/2004 | Balbierz | |
| 6,772,014 B2 | 8/2004 | Coe et al. | |
| 6,836,687 B2 | 12/2004 | Kelley et al. | |
| 6,856,835 B2 * | 2/2005 | Bardy | A61N 1/375 607/14 |
| 6,866,044 B2 | 3/2005 | Bardy et al. | |
| 6,868,291 B1 | 3/2005 | Bonner et al. | |
| 6,887,229 B1 | 5/2005 | Kurth | |
| 6,890,295 B2 | 5/2005 | Michels et al. | |
| 6,999,819 B2 | 2/2006 | Swoyer et al. | |
| 7,033,326 B1 | 4/2006 | Pianca et al. | |
| 7,050,851 B2 | 5/2006 | Plombon et al. | |
| 7,069,083 B2 | 6/2006 | Finch et al. | |
| 7,096,064 B2 | 8/2006 | Deno et al. | |
| 7,117,039 B2 | 10/2006 | Manning et al. | |
| 7,195,637 B2 | 3/2007 | Mika | |
| 7,218,970 B2 | 5/2007 | Ley et al. | |
| 7,225,034 B2 | 5/2007 | Ries et al. | |
| 7,229,450 B1 | 6/2007 | Chitre et al. | |
| 7,272,448 B1 | 9/2007 | Morgan et al. | |
| 7,288,096 B2 * | 10/2007 | Chin | A61B 17/3468 606/108 |
| 7,316,667 B2 | 1/2008 | Lindstrom et al. | |
| 7,322,960 B2 | 1/2008 | Yamamoto et al. | |
| 7,369,899 B2 | 5/2008 | Malinowski et al. | |
| 7,389,134 B1 | 6/2008 | Karicherla et al. | |
| 7,392,085 B2 | 6/2008 | Warren et al. | |
| 7,450,997 B1 | 11/2008 | Pianca et al. | |
| 7,496,408 B2 | 2/2009 | Ghanem et al. | |
| 7,499,758 B2 | 3/2009 | Cates et al. | |
| 7,539,542 B1 | 5/2009 | Malinowski | |
| 7,627,375 B2 | 12/2009 | Bardy et al. | |
| 7,655,014 B2 | 2/2010 | Ko et al. | |
| 7,684,864 B2 * | 3/2010 | Olson | A61N 1/375 607/36 |
| 7,736,330 B2 | 6/2010 | Bardy | |
| 7,761,150 B2 | 7/2010 | Ghanem et al. | |
| 7,765,014 B2 | 7/2010 | Eversull et al. | |
| 7,801,622 B2 | 9/2010 | Camps et al. | |
| 7,837,671 B2 | 11/2010 | Eversull et al. | |
| 7,846,088 B2 | 12/2010 | Ness | |
| 7,850,610 B2 | 12/2010 | Ferek-Petric | |
| 7,890,191 B2 | 2/2011 | Rutten et al. | |
| 7,908,015 B2 | 3/2011 | Lazeroms et al. | |
| 7,920,915 B2 | 4/2011 | Mann et al. | |
| 7,930,028 B2 | 4/2011 | Lang et al. | |
| 7,930,040 B1 | 4/2011 | Kelsch et al. | |
| 7,983,765 B1 | 7/2011 | Doan et al. | |
| 8,060,207 B2 | 11/2011 | Wallace et al. | |
| 8,065,020 B2 | 11/2011 | Ley et al. | |
| 8,066,702 B2 | 11/2011 | Rittman, III et al. | |
| 8,090,451 B2 | 1/2012 | Tyson, Jr. | |
| 8,155,755 B2 | 4/2012 | Flynn et al. | |
| 8,157,813 B2 | 4/2012 | Ko et al. | |
| 8,165,696 B2 * | 4/2012 | McClure | A61N 1/3605 607/116 |
| 8,260,436 B2 | 9/2012 | Gerber et al. | |
| 8,280,527 B2 | 10/2012 | Eckerdal et al. | |
| 8,340,779 B2 | 12/2012 | Harris et al. | |
| 8,355,786 B2 | 1/2013 | Malinowski | |
| 8,386,052 B2 | 2/2013 | Harris et al. | |
| 8,394,079 B2 | 3/2013 | Drake et al. | |
| 8,435,208 B2 | 5/2013 | Bardy | |
| 8,442,620 B2 | 5/2013 | Silipo et al. | |
| 8,452,421 B2 | 5/2013 | Thenuwara et al. | |
| 8,478,424 B2 | 7/2013 | Tronnes | |
| 8,478,426 B2 | 7/2013 | Barker | |
| 8,594,809 B2 | 11/2013 | Yang et al. | |
| 8,886,311 B2 | 11/2014 | Anderson et al. | |
| 9,126,031 B2 | 9/2015 | Tekmen et al. | |
| 2002/0049476 A1 | 4/2002 | Bardy et al. | |
| 2002/0120294 A1 | 8/2002 | Kroll | |
| 2003/0088278 A1 | 5/2003 | Bardy et al. | |
| 2003/0114908 A1 | 6/2003 | Flach | |
| 2004/0059348 A1 | 3/2004 | Geske et al. | |
| 2004/0102829 A1 | 5/2004 | Bonner et al. | |
| 2004/0143284 A1 | 7/2004 | Chin | |
| 2004/0210293 A1 | 10/2004 | Bardy et al. | |
| 2004/0215240 A1 | 10/2004 | Lovett et al. | |
| 2004/0215308 A1 | 10/2004 | Bardy et al. | |
| 2004/0230279 A1 | 11/2004 | Cates et al. | |
| 2004/0230280 A1 | 11/2004 | Cates et al. | |
| 2004/0230281 A1 | 11/2004 | Heil et al. | |
| 2004/0230282 A1 | 11/2004 | Cates et al. | |
| 2004/0236396 A1 | 11/2004 | Coe et al. | |
| 2005/0049663 A1 | 3/2005 | Harris et al. | |

(56) References Cited

U.S. PATENT DOCUMENTS

| | | |
|---|---|---|
| 2005/0131505 A1 | 6/2005 | Yokoyama |
| 2005/0277990 A1 | 12/2005 | Ostroff et al. |
| 2005/0288758 A1 | 12/2005 | Jones et al. |
| 2006/0041295 A1 | 2/2006 | Okypka |
| 2006/0116746 A1 | 6/2006 | Chin |
| 2006/0122676 A1 | 6/2006 | Ko et al. |
| 2006/0136004 A1* | 6/2006 | Cowan ............... A61N 1/37205 607/33 |
| 2006/0161205 A1 | 7/2006 | Mitrani et al. |
| 2006/0247753 A1 | 11/2006 | Wenger et al. |
| 2006/0253181 A1 | 11/2006 | Schulman et al. |
| 2006/0265018 A1* | 11/2006 | Smith .................... A61N 1/372 607/14 |
| 2007/0023947 A1 | 2/2007 | Ludwig et al. |
| 2007/0049975 A1 | 3/2007 | Cates et al. |
| 2007/0088394 A1 | 4/2007 | Jacobson |
| 2007/0100409 A1 | 5/2007 | Worley et al. |
| 2007/0179388 A1 | 8/2007 | Larik et al. |
| 2007/0208402 A1 | 9/2007 | Helland et al. |
| 2007/0249992 A1 | 10/2007 | Bardy |
| 2008/0046056 A1 | 2/2008 | O'Connor |
| 2008/0243219 A1 | 10/2008 | Malinowski et al. |
| 2008/0269716 A1 | 10/2008 | Bonde et al. |
| 2009/0157091 A1 | 6/2009 | Buysman |
| 2009/0222021 A1 | 9/2009 | Chang |
| 2009/0259283 A1 | 10/2009 | Brandt et al. |
| 2009/0264780 A1 | 10/2009 | Schilling |
| 2009/0270962 A1 | 10/2009 | Yang et al. |
| 2010/0016935 A1 | 1/2010 | Strandberg et al. |
| 2010/0030227 A1 | 2/2010 | Kast et al. |
| 2010/0030228 A1 | 2/2010 | Havel |
| 2010/0042108 A1 | 2/2010 | Hibino |
| 2010/0056858 A1 | 3/2010 | Mokelke et al. |
| 2010/0094252 A1 | 4/2010 | Wengreen et al. |
| 2010/0113963 A1 | 5/2010 | Smits et al. |
| 2010/0125194 A1 | 5/2010 | Bonner et al. |
| 2010/0137879 A1 | 6/2010 | Ko et al. |
| 2010/0152747 A1 | 6/2010 | Padiy et al. |
| 2010/0152798 A1 | 6/2010 | Sanghera et al. |
| 2010/0211064 A1 | 8/2010 | Mahapatra et al. |
| 2010/0217298 A1 | 8/2010 | Bardy |
| 2010/0217301 A1 | 8/2010 | Bardy |
| 2010/0241185 A1 | 9/2010 | Mahapatra et al. |
| 2010/0249696 A1 | 9/2010 | Bardy |
| 2010/0305428 A1 | 12/2010 | Bonner et al. |
| 2010/0318098 A1 | 12/2010 | Lund et al. |
| 2011/0009933 A1 | 1/2011 | Barker |
| 2011/0077708 A1 | 3/2011 | Ostroff |
| 2011/0125163 A1 | 5/2011 | Rutten et al. |
| 2011/0224680 A1 | 9/2011 | Barker |
| 2011/0224681 A1 | 9/2011 | McDonald |
| 2011/0257660 A1 | 10/2011 | Jones et al. |
| 2012/0016377 A1 | 1/2012 | Geroy |
| 2012/0029335 A1 | 2/2012 | Sudam et al. |
| 2012/0078266 A1 | 3/2012 | Tyson, Jr. |
| 2012/0089153 A1 | 4/2012 | Christopherson et al. |
| 2012/0097174 A1 | 4/2012 | Spotnitz et al. |
| 2012/0123496 A1 | 5/2012 | Schotzko et al. |
| 2012/0191106 A1 | 7/2012 | Ko et al. |
| 2012/0209283 A1 | 8/2012 | Zhu |
| 2012/0209285 A1 | 8/2012 | Barker et al. |
| 2012/0220849 A1* | 8/2012 | Brockway ............ A61N 1/0504 600/374 |
| 2012/0316613 A1* | 12/2012 | Keefe .................. A61N 1/3962 607/17 |
| 2013/0041345 A1 | 2/2013 | Kilcoin et al. |
| 2013/0103049 A1 | 4/2013 | Bonde |
| 2013/0158564 A1 | 6/2013 | Harris et al. |
| 2013/0238067 A1 | 9/2013 | Baudino |
| 2014/0330325 A1 | 11/2014 | Thompson-Nauman et al. |
| 2014/0330326 A1 | 11/2014 | Thompson-Nauman et al. |
| 2014/0330327 A1 | 11/2014 | Thompson-Nauman et al. |
| 2014/0330329 A1 | 11/2014 | Thompson-Nauman et al. |
| 2014/0330331 A1 | 11/2014 | Thompson-Nauman et al. |

FOREIGN PATENT DOCUMENTS

| | | |
|---|---|---|
| EP | 1541191 A1 | 6/2005 |
| JP | 2007500549 A | 1/2007 |
| WO | 2001023035 A1 | 4/2001 |
| WO | 0226315 A1 | 4/2002 |
| WO | 2004073506 A2 | 9/2004 |
| WO | 2005011809 A2 | 2/2005 |
| WO | 20100047893 A1 | 4/2010 |

OTHER PUBLICATIONS

Ganapathy et al., "Implantable Device to Monitor Cardiac Activity with Sternal Wires," Pace, vol. 37, Dec. 2014, 11 pages.

Guenther et al., "Substernal Lead Implantation: A Novel Option to Manage DFT Failure in S-ICD patients," Clinical Research Cardiology, Published On-line Oct. 2, 2014, 3 pages.

Tung et al., "Initial Experience of Minimal Invasive Extra Cardiac Placement of High Voltage Defibrillator Leads," Canadian Cardiovascular Congress 2007, Oct. 2007, vol. 23, Supplement SC, Abstract 0697, http://www.pulsus.com/ccc2007/abs/0697.htm, 2 pages.

Alexander et al., "Implications of Implantable Cardioverter Defibrillator Therapy in Congenital Heart Disease and Pediatrics", Journal of Cardiovascular Electrophysiology, vol. 15, No. 1, Jan. 2004, 5 pages.

Baddour et al., Update on Cardiovascular Implantable Electronic Device Infections and Their Management—A Scientific Statement from the American Heart Association, Circulation available at http://circ.ahajournals.org, Jan. 26, 2010; 23 pages.

Bauersfeld et al., "Initial Experience With Implantable Cardioverter Defibrillator Systems Using Epicardial and Pleural Electrodes in Pediatric Patients", The Annals of Thoracic Surgery, 2007, vol. 84, 3 pages.

Berul et al., "Minimally Invasive Cardioverter Defibrillator Implantation for Children: An Animal Model and Pediatric Case Report", Journal of Pacing and Clinical Electrophysiology, Dec. 2001, vol. 24, No. 12, 6 pages.

Hsia et al., "Novel Minimally Invasive, Intrapericardial Implantable Cardioverter Defibrillator Coil System: A Useful Approach to Arrhythmia Therapy in Children", The Annals of Thoracic Surgery, 2009, vol. 87, 6 pages.

Tung et al., Invention Disclosure Form for "Hybrid Endovascular and Extrvascular Implantable Cardioverter-Defibrillator System", Mar. 2006, 10 pages.

Cooper et al., "Implantable Cardioverter Defibrillator Lead Complications and Laser Extraction in Children and Young Adults With Congenital Heart Disease: Implications for Implantation and Management", Journal of Cardiovascular Electrophysiology, vol. 14, No. 4, Apr. 2003, 7 pages.

Obadia, et al., "New Approach for Implantation of Automatic Defibrillators Using Videothoracoscopy", Journal Ann Cardiol Angeiol (Paris); Sep. 1994; 43 (7) Abstract Only, 1 page.

Lemmer, "Defibrillator Patch Constriction, Letter to the Editor", The Annals of Thoracic Surgery, 1996, 1 page.

Ely et al., "Thoracoscopic Implantation of the Implantable Cardioverter Defibrillator", Minimally Invasive Techniques; (Can be found on the World-Wide Web at http://chestioumal.chestpubs.org on May 6, 2013); dated Jan. 1993; 2 pages.

Damiano, "Implantation of Cardioverter Defibrillators in the Post-Sternotomy Patient", The Annals of Thoracic Surgery, 1992; 53: pp. 978-983.

Piccione, et al., "Erosion of Extrapericardial Implantable Cardioverter Defibrillator Patch Through the Gastic Fundus with Fistulous Tract Information", Cardiology in Review; 2006; 14, e21-e23 pages.

Vyhmeister et al., "Simple Approach for Extrapericardial Placement of Defibrillator Patches via Median Sternotomy", The Annals of Thoracic Surgery; 1994; 57: 4 pages.

Harman et al., "Differences in the Pathological Changes in Dogs' Hearts After Defibrillation with Extrapericardial Paddles and Implanted Defibrillator Electrodes", Journal of Pacing and Clinical Electrophysiology, Feb. 1991; vol. 14; Part 2; 5 pages.

(56) References Cited

OTHER PUBLICATIONS

Obadia et al., "Thoracoscopic Approach to Implantable Cardioverter Defibrillator Patch Electrode Implantation", Pacing and Clinical Electrophysiology; Jun. 1996; vol. 19; 6 pages.
Shapira, et al., "A Simplied Method for Implantation of Automatic Cardioverter Defibrillator in Patients with Previous Cardiac Surgery", Pacing and Clinical Electrophysiology, January Part I, 1993, vol. 16; 6 pages.
Quigley et al., "Migration of an Automatic Implantable Cardioverter-Defibrillator Patch Causing Massive Hemothorax", Journal Texas Heart Institute, Nov. 1, 1996; vol. 23, 4 pages.
Karwande et al., "Bilateral Anterior Thoracotomy for Automatic Implantable Cardioverter Defibrillator Placement in Patients with Previous Sternotomy", The Annals of Thoracic Surgery; Oct. 1992; 54(4); 3 pages.
Bielefeld et al., "Thoracoscopic Placement of Implantable Cardioverter-Defibrillator Patch Leads in Sheep", Circulation; Nov. 1993, vol. 88, No. 5, Part 2; 5 pages.
Frame et al., "Long-Term Stability of Defibrillation Thresholds with Intrapericardial Defibrillator Patches", Pacing and Clinical Electrophysiology, Jan. 1993, Part II, vol. 16, 6 pages.
Lawrie et al., "Right Mini-Thoracotomy: An Adjunct to Left Subcostal Automatic Implantable Cardioverter Defibrillator Implantation", The Annals of Thoracic Surgery; 1989; 47; 4 pages.
Mitchell et al., "Experience with an Implantable Tiered Therapy Device Incorporating Antitachycardia Pacing and Cardioverter/Defibrillator Therapy", Thoracic and Cardiovascular Surgery, Abstract Only, Mar. 1993, 1 page.
Bolling et al., "Automatic Internal Cardioverter Defibrillator: A Bridge to Heart Transplantation", Heart Lung Transplantation, Abstract Only, Jul.-Aug. 1991, 1 page.
Steinke et al., "Subepicardial Infarction, Myocardial Impression, and Ventricular Penetration by Sutureless Electrode and Leads", Chest; 70: 1, Jul. 1976, 2 pages.
Avogadros Lab Supply Inc., Catalog; Scoopula with Beech Wood Handle, can be found on-line at http://www.avogadro-lab-supply.com/search.php, accessed Oct. 6, 2013, 1 page.
Medtronic, Inc. 6996SQ Subcutaneous, Unipolar Lead with Defibrillation Coil Electrode, Technicial Manual, 22 pages.
Medtronic, Inc. 6996T Tunneling Tool, Technical Manual, 12 pages.
Pebax Product Brochure, 14 pages and can be found on-line at http://www.pebax.com/export/sites/pebax/.content/medias/downloads/literature/pebax-product-range-brochure.pdf, 14 pages.
Cigna et al., "A New Technique for Substernal Colon Transposition with a Breast Dissector: Report of 39 Cases", Journal of Plastic, Reconstructive and Aesthetic Surgery, 2006:59, 4 pages.
Tung et al., "Minimal Invasive Extra Cardiac Placement of High Voltage Defibrillator Leads", Poster 3; S200 Abstract, PO-3-4; St. Paul Hospital, Vancouver, British Columbia, Canada, 1 pages.
Molina et al, "An Epicardial Subxiphoid Implantable Defibrillator Lead: Superior Effectiveness After Failure of Stndard Implants", From the Department of Surgery, Division of Cardiovascular and Thoracic Surgery and the Department of Medicine, Cardiac Arrhymthmia Center, University of Minnesota Medical School, Minneapolis, Minnesota, Pace, vol. 27, Nov. 2004, 7 pages.
Baudoin et al., The Superior Epigastric Artery Does Not Pass Through Larrey's Space (Trigonum Sternocostale) Surgical Radiol Anat (2003), 25: 259-262.
Haydin et al., "Subxiphoid Approach to Epicardial Implantation of Implantable Cardioverter Defibrillators in Children", PACE, vol. 36, Aug. 2013, 5 pages.
Falk et al., "External Cardiac Pacing Using Low Impedance Electrodes Suitable for Defibrillation: A Comparative Blinded Study," Journal of American College of Cardiology, vol. 22, No. 5, Nov. 1, 1993, 5 pages.
Laudon, M. K., "Pulse Output", Chapter 11 of Design of Pacemakers, Published by the Institute of Electrical and Electronics Engineers, Inc., New York,(1995), 30 pages.
Restriction Requirement from U.S. Appl. No. 14/261,456, dated May 25, 2016, 8 pp.
Response to Restriction Requirement dated May 25, 2016, from U.S. Appl. No. 14/261,456, filed Jul. 22, 2016, 2 pp.
Office Action from U.S. Appl. No. 14/261,456, dated Oct. 11, 2016, 5 pp.
Restriction Requirement from U.S. Appl. No. 14/261,460, dated May 13, 2016, 7 pp.
Response to Restriction Requirement dated May 13, 2016, from U.S. Appl. No. 14/261,460, filed Jul. 13, 2016, 2 pp.
Office Action from U.S. Appl. No. 14/261,460, dated Oct. 14, 2016, 4 pp.
Restriction Requirement from U.S. Appl. No. 14/261,479, dated May 25, 2016, 7 pp.
Response to Restriction Requirement dated May 25, 2016, from U.S. Appl. No. 14/261,479, filed Jul. 22, 2016, 1 pp.
Office Action from U.S. Appl. No. 14/261,479, dated Oct. 7, 2016, 5 pp.
Restriction Requirement from U.S. Appl. No. 14/261,470, dated Apr. 28, 2016, 8 pp.
Response to Restriction Requirement dated Apr. 28, 2016, from U.S. Appl. No. 14/261,470, filed May 3, 2016, 2 pp.
Office Action from U.S. Appl. No. 14/261,470, dated Aug. 12, 2016, 5 pp.
"SQ-RX Pulse Generator, A Component of the S-ICD System," User's Manual, Model 1010, Cameron Health, Inc., Dec. 2, 2008, 46 pp.
Erickson, MD., "Non-thoracotomy ICD Implantation in Pediatric and Adult Congenital Heart Disease Patients," Oct. 2015, 44 slides.
Office Action, in the Chinese language, from Chinese Application No. 201480025740.9, dated Sep. 27, 2016, 9 pp.
First Office Action and Search Report, and translation thereof, from counterpart Chinese Application No. 201480035082.1, dated Sep. 27, 2016, 29 pp.
First Office Action and Search Report, and translation thereof, from counterpart Chinese Application No. 201480025657.1, dated Oct. 8, 2016, 24 pp.
Response to Office Action dated Oct. 11, 2016, from U.S. Appl. No. 14/261,456, filed Jan. 10, 2017, 17 pp.
Response to Office Action dated Oct. 14, 2016, from U.S. Appl. No. 14/261,460, filed Jan. 10, 2017, 9 pp.
Response to Office Action dated Nov. 2, 2016, from U.S. Appl. No. 14/261,479, filed Feb. 2, 2017, 12 pp.
Response to Office Action dated Aug. 12, 2016, from U.S. Appl. No. 14/261,470, filed Nov. 14, 2016, 12 pp.
Amendment in Response to Office Action dated Mar. 3, 2017, from U.S. Appl. No. 14/261,470, filed Jun. 5, 2017, 13 pp.
Notice of Allowance from U.S. Appl. No. 14/261,460, dated May 11, 2017, 7 pp.
Final Office Action from U.S. Appl. No. 14/261,456, dated May 5, 2017, 6 pp.
Final Office Action from U.S. Appl. No. 14/261,479, dated May 18, 2017, 6 pp.
Final Office Action from U.S. Appl. No. 14/261,470, dated Jul. 3, 2017, 8 pp.
Amendment in Response to Office Action dated May 5, 2017, from U.S. Appl. No. 14/261,456, filed Jul. 5, 2017, 18 pp.
Amendment in Response to Office Action dated May 18, 2017, from U.S. Appl. No. 14/261,479, filed Jul. 18, 2017, 14 pp.
Response to Final Office Action dated Jul. 3, 2017, from U.S. Appl. No. 14/261,470, filed Sep. 5, 2017, 6 pp.
Advisory Action from U.S. Appl. No. 14/261,456, dated Aug. 30, 2017, 3 pp.
Notice of Appeal from U.S. Appl. No. 14/261,456, filed Aug. 30, 2017, 1 pp.
Advisory Action from U.S. Appl. No. 14/261,479, dated Aug. 8, 2017, 3 pp.
Advisory Action from U.S. Appl. No. 14/261,470, dated Sep. 18, 2017, 3 pp.
Final Rejection from U.S. Appl. No. 14/261,470, dated Oct. 4, 2017, 10 pp.
Response to Final Office Action dated Oct. 4, 2017, from U.S. Appl. No. 14/261,470, filed Dec. 4, 2017, 17 pp.
Appeal Brief from U.S. Appl. No. 14/261,456, filed Oct. 30, 2017, 32 pp.

(56) References Cited

OTHER PUBLICATIONS

Office Action from U.S. Appl. No. 14/261,479, dated Oct. 12, 2017, 10 pp.

Sgoifo et al., "Electrode Positioning for Reliable Telemetry ECG Recordings During Social Stress in Unrestrained Rats" Physiology and Behaviours, vol. 60, issue 6, Dec. 1996, pp. 1397-1401.

Office Action from U.S. Appl. No. 14/61,456, dated Mar. 9, 2018, 7 pp.

Office Action from U.S. Appl. No. 14/261,470, dated Mar. 26, 2018, 10 pp.

Response to Office Action dated Jan. 12, 2018, from U.S. Appl. No. 15/661,365, filed Apr. 5, 2018, 14 pp.

Final Office Action from U.S. Appl. No. 14/261,479, dated Jul. 13, 2018, 9 pp.

Thompson-Nauman et al., "Implantable Cardioverter-Defibrillator (ICD) System Including Substernal Lead", JP Patent Application No. 2016-512987, Japanese Office Action dated Feb. 2, 2018, 4 pages.

Advisory Action from U.S. Appl. No. 14/261,470, dated Jan. 12, 2018, 3 pp.

Response to Office Action dated Oct. 12, 2017, from U.S. Appl. No. 14/261,479, filed Feb. 12, 2018, 19 pp.

Office Action from U.S. Appl. No. 15/661,365, dated Jan. 12, 2018, 5 pp.

Thompson-Nauman et al., Implantable Cardioverter-Defibrillator (ICD) System Including Substernal Pacing Lead, Notice of Third Office Action, Chinese Patent Application No. 201480025657.1, Dispatched Jan. 2, 2018, 20 pages.

Response to Office Action dated Mar. 9, 2018, from U.S. Appl. No. 14/261,456, filed Jun. 4, 2018, 15 pp.

Response to Office Action dated Mar. 26, 2018, from U.S. Appl. No. 14/261,470, filed Jun. 26, 2018, 18 pp.

Final Rejection from U.S. Appl. No. 15/661,365, dated Sep. 24, 2018, 8 pp.

Final Rejection from U.S. Appl. No. 14/261,479, dated Jul. 13, 2018, 9 pp.

Office Action from U.S. Appl. No. 14/261,479, dated Sep. 12, 2018, 17 pp.

Final Office Action from U.S. Appl. No. 14/261,470, dated Dec. 3, 2018, 12 pp.

Final Office Action from U.S. Appl. No. 14/261,456, dated Nov. 8, 2018, 12 pp.

Final Office Action from U.S. Appl. No. 15/661,365, dated Jan. 2, 2019, 11 pp.

Response to Final Office Action dated Sep. 24, 2018, from U.S. Appl. No. 15/661,365, filed Nov. 26, 2018, 17 pp.

Advisory Action from U.S. Appl. No. 14/261,479, dated Jan. 22, 2019, 3 pp.

Response to Final Office Action dated Sep. 18, 2018, from U.S. Appl. No. 14/261,479, filed Nov. 19, 2018, 12 pp.

Office Action from U.S. Appl. No. 14/261,470, dated Mar. 3, 2017, 7 pp.

Notice of Allowance from U.S. Appl. No. 15/661,365, dated Jul. 29, 2019, 8 pp.

Notice of Allowance from U.S. Appl. No. 15/661,365, dated Aug. 27, 2019, 5 pp.

Notice of Allowance from U.S. Appl. No. 14/261,470, dated Jul. 17, 2019, 7 pp.

Notice of Allowance from U.S. Appl. No. 14/261,470, dated Sep. 11, 2019, 5 pp.

Notice of Allowance from U.S. Appl. No. 14/261,456, dated Jul. 17, 2019, 8 pp.

Notice of Allowance from U.S. Appl. No. 14/261,456, dated Sep. 13, 2019, 5 pp.

Notice of Allowance from U.S. Appl. No. 14/261,479, dated Aug. 27, 2019, 5 pp.

Notice of Allowance from U.S. Appl. No. 14/261,479, dated Jul. 11, 2019, 8 pp.

Appeal Brief from U.S. Appl. No. 14/261,470, filed Apr. 29, 2019, 39 pp.

Appeal Brief from U.S. Appl. No. 14/261,456, filed Apr. 8, 2019, 40 pp.

Appeal Brief from U.S. Appl. No. 14/261,479, filed Mar. 22, 2019, 37 pp.

Appeal Brief from U.S. Appl. No. 15/661,365, filed Jun. 3, 2019, 17 pp.

\* cited by examiner

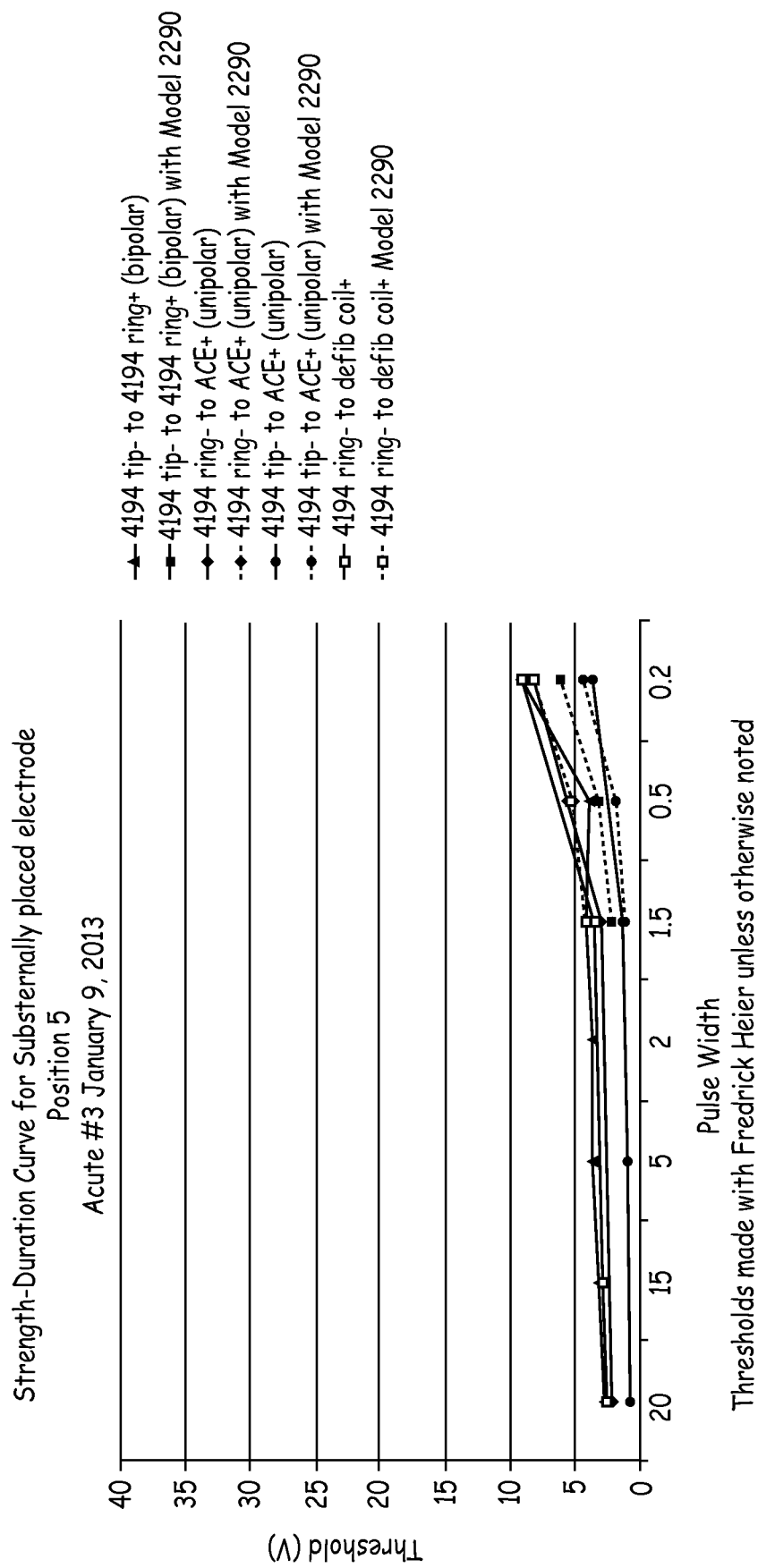

SUBSTERNAL LEADLESS ELECTRICAL STIMULATION SYSTEM

This application claims the benefit of U.S. Provisional Application No. 61/820,033, filed on May 6, 2013, the content of which is incorporated herein by reference in its entirety.

FIELD OF THE INVENTION

The present application relates to leadless electrical stimulation devices, systems and methods for providing substernal electrical stimulation, including substernal cardiac pacing.

BACKGROUND OF THE INVENTION

Implantable pulse generators have been utilized to provide electrical stimulation to various organs, tissues, muscle, nerves or other features of a patient's body. One example of electrical stimulation provided to a patient is cardiac pacing. Cardiac pacing electrically stimulates the heart when the heart's natural pacemaker and/or conduction system fails to provide synchronized atrial and ventricular contractions at appropriate rates and intervals for a patient's needs. When a patient's heart is beating too slow, bradycardia pacing increases the rate at which the patient's heart contracts to provide relief from symptoms associated with bradycardia. Cardiac pacing may also provide electrical overdrive stimulation intended to suppress or convert tachyarrhythmias, again supplying relief from symptoms and preventing or terminating arrhythmias that could lead to sudden cardiac death or need to be treated with high voltage defibrillation or cardioversion shocks.

Pacemakers typically require at least two electrodes to deliver electrical stimulation therapy to the heart and to sense electrical activity of the heart. Traditionally, pacemaker systems are comprised of an implantable pulse generator (or pacemaker) coupled to one or more leads. The lead(s) include one or more electrodes on a distal portion of the lead that are implanted inside the heart such that at least one electrode touches the endocardium. In other examples, the one or more leads can be implanted on the epicardial surface of the heart. In still further examples, leadless pacing devices may be implanted within one or more chambers of the heart and provide pacing pulses to the heart.

SUMMARY OF THE INVENTION

The present application is directed to implantable cardiac pacing systems and methods for providing substernal pacing. In one embodiment, an implantable cardiac pacing system includes a housing, a first electrode on the housing, a second electrode on the housing, and a pulse generator within the housing and electrically coupled to the first electrode and the second electrode, wherein the housing is implanted substantially within an anterior mediastinum of a patient and the pulse generator is configured to deliver pacing pulses to a heart of the patient via a therapy vector formed between the first and second electrodes.

In another embodiment, a method comprises providing a leadless implantable pulse generator (IPG) substantially within an anterior mediastinum of a patient, the leadless IPG including a housing, first electrode on the housing, a second electrode on the housing, and an pulse generator within the housing and electrically coupled to the first electrode and the second electrode, generating one or more stimulation pulses with the implantable pulse generator, and delivering the one or more stimulation pulses to a heart of the patient via the first and second electrode of the leadless IPG implanted substantially within the anterior mediastinum.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

BRIEF DESCRIPTION OF THE DRAWINGS

FIG. 10 is a graph illustrating strength-duration curves of electrical data from a third acute experiment.

DETAILED DESCRIPTION

Figure 1A:
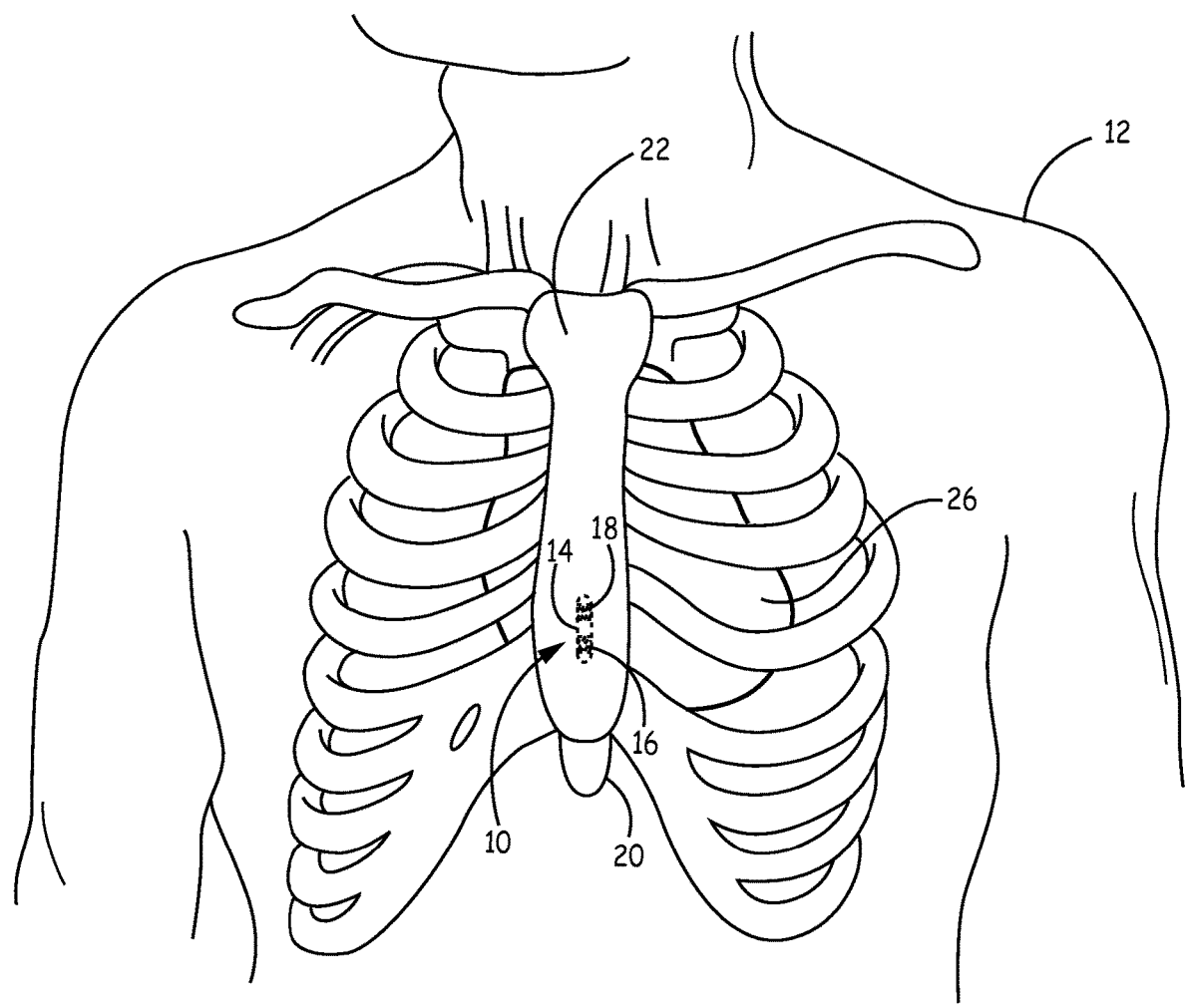
FIG. 1A is a front view of an example leadless IPG implanted within a patient.
Figure 1B:
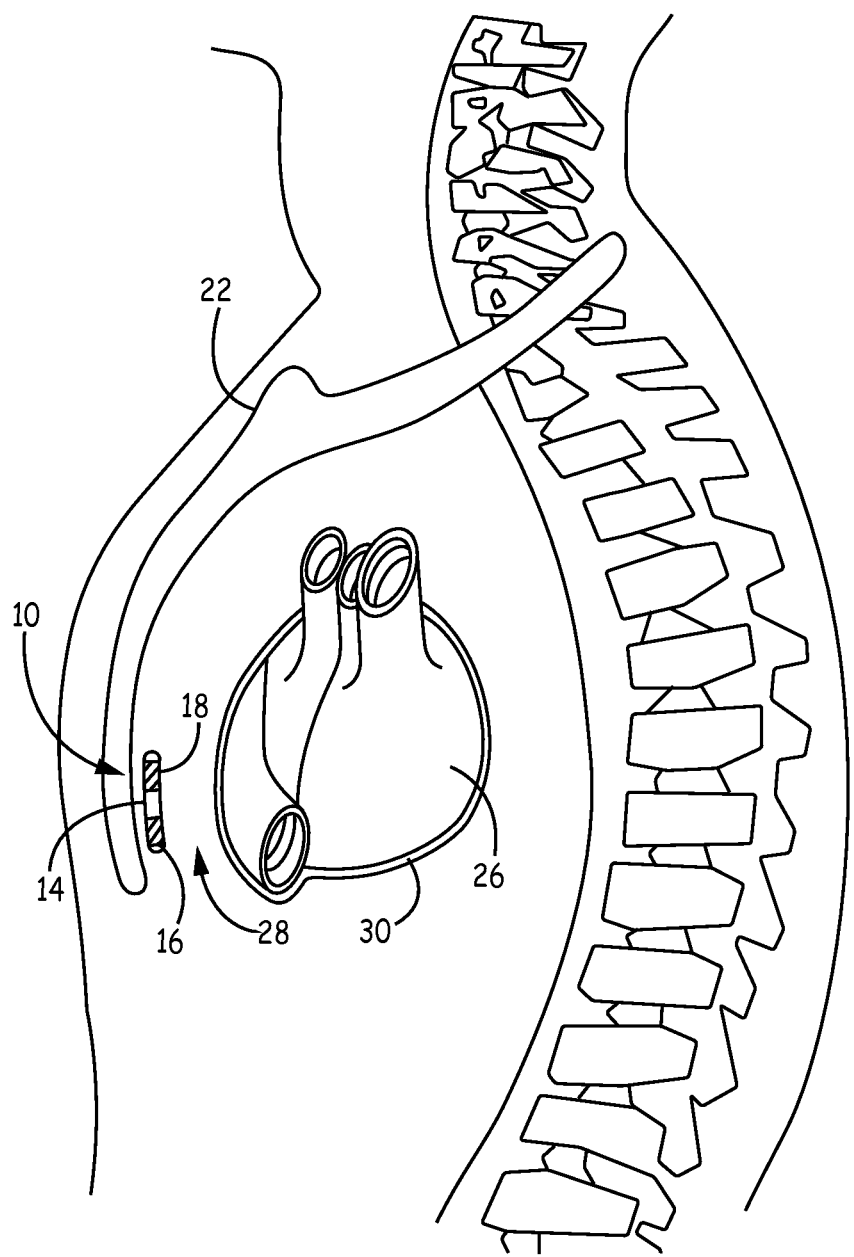
FIG. 1B is a side view of an example leadless IPG implanted within a patient.
Figure 1C:
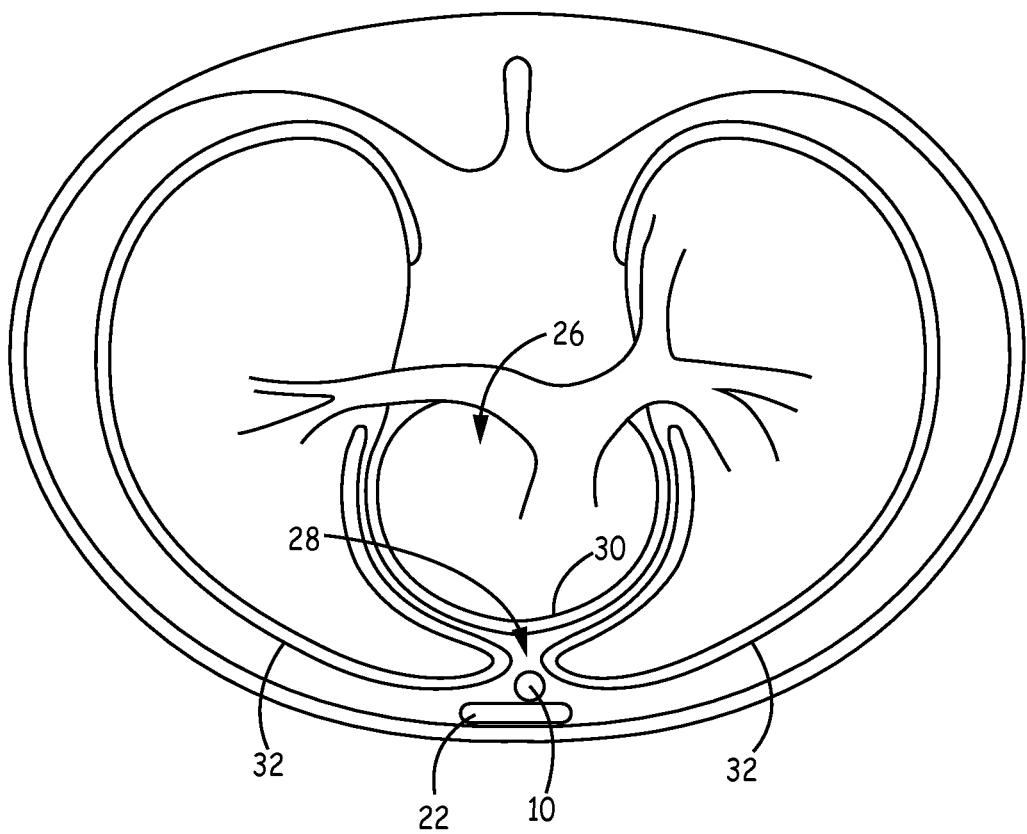
FIG. 1C is a transverse view of an example leadless IPG implanted within a patient.

FIGS. 1A-C are conceptual diagrams of an example leadless implantable pulse generator (IPG) 10 implanted within a patient 12. FIG. 1A is a front view of patient 12 implanted with leadless IPG 10. FIG. 1B is a side view of patient 12 with leadless IPG 10. FIG. 1C is a transverse view of patient 12 with leadless IPG 10. FIGS. 1A-C are described in the context of implantable cardiac pacing. However, the techniques of this disclosure may also be used in the context of other implantable medical devices configured to provide electrical stimulation pulses to stimulate other organs, tissues, muscles, or nerves within the body of patient 12. For example, leadless IPG 10 implanted in the manner described herein may provide electrical stimulation pulses to stimulate nerves, skeletal muscles, diaphragmatic muscles, e.g., for various neuro-cardiac applications and/or for apnea or respiration therapy.

Leadless IPG 10 is implanted underneath/below sternum 22 substantially within anterior mediastinum 28. Anterior mediastinum 28 may be viewed as being bounded laterally by pleurae 32, posteriorly by pericardium 30, and anteriorly by sternum 22. In some instances, the anterior wall of anterior mediastinum 28 may also be formed by the transversus thoracis and one or more costal cartilages. Anterior mediastinum 28 includes a quantity of loose connective tissue (such as areolar tissue), some lymph vessels, lymph glands, substernal musculature (e.g., transverse thoracic muscle), branches of the internal thoracic artery, and the internal thoracic vein. For example, leadless IPG 10 may be implanted substantially within the loose connective tissue and/or substernal musculature of anterior mediastinum 28. A leadless IPG implanted substantially within anterior mediastinum 28 will be referred to herein as a substernal leadless IPG. Also, electrical stimulation, such as pacing, provided by a leadless IPG implanted substantially within anterior mediastinum 28 will be referred to herein as substernal electrical stimulation or substernal pacing.

Although leadless IPG 10 is described herein as being implanted substantially within anterior mediastinum 28, leadless IPG 10 may be implanted in other non-vascular, extra-pericardial locations, including the gap, tissue, or other anatomical features around the perimeter of and adjacent to, but not attached to, the pericardium or other portion of heart 26 and not above sternum 22 or ribcage. As such, leadless IPG 10 may be implanted anywhere within the "substernal space" defined by the undersurface between the sternum and/or ribcage and the body cavity but not including the pericardium or other portion of heart 26. The substernal space may alternatively be referred to by the terms "retrosternal space" or "mediastinum" or "infrasternal" as is known to those skilled in the art and includes the anterior mediastinum 28. The substernal space may also include the anatomical region described in Baudoin, Y. P., et al., entitled "The superior epigastric artery does not pass through Larrey's space (trigonum sternocostale)." Surg. Radiol. Anat. 25.3-4 (2003): 259-62 as Larrey's space. In other words, leadless IPG 10 may be implanted in the region around the outer surface of heart 26, but not attached to heart 26.

Leadless IPG 10 includes a housing 14 having electrodes 16 and 18. Leadless IPG 10 may be implanted substantially within anterior mediastinum 28 such that leadless IPG 10 can sense electrical activity of heart 26 and/or deliver electrical stimulation, e.g., pacing, to heart 26 via electrodes 16 and 18. In one example, leadless IPG 10 may be implanted such that electrodes 16 and 18 are located substantially over a cardiac silhouette of one or both ventricles as observed via an anterior-posterior (AP) fluoroscopic view of heart 26. In another example leadless IPG 10 may be implanted such that a bipolar therapy vector between electrodes 16 and 18 is centered or otherwise located over the ventricle(s). However, leadless IPG 10 may be positioned at other locations as long as the bipolar therapy vector between electrodes 16 and 18 result in capture of the ventricle(s) of heart 26.

In the example illustrated in FIGS. 1A-C, leadless IPG 10 is located substantially centered under sternum 22. In other instances, however, leadless IPG 10 may be implanted such that it is offset laterally from the center of sternum 22. In some instances, leadless IPG 10 may extend laterally enough such that all or a portion of leadless IPG 10 is underneath/below the ribcage in addition to or instead of sternum 22.

Additionally, although leadless IPG 10 is described in the context of providing ventricular pacing, leadless IPG 10 may be placed to provide atrial pacing. In this case, leadless IPG 10 may be positioned further superior within anterior mediastinum 28 such that leadless IPG 10 can deliver electrical stimulation, e.g., pacing, to an atrium of heart 26 via electrodes 16 and 18. For example, leadless IPG 10 may be positioned within anterior mediastinum 28 such that electrodes 16 and 18 are located over the atrium as observed in an AP fluoroscopic view of heart 26 and/or such that the bipolar therapy vector between electrodes 16 and 18 is substantially over the atrium or otherwise capable of capturing the atrium of heart 26.

In addition, it should be noted that leadless IPG 10 may not be limited to treatment of a human patient. In alternative examples, leadless IPG 10 may be implemented in non-human patients, e.g., primates, canines, equines, pigs, ovines, bovines and felines. These other animals may undergo clinical or research therapies that may benefit from the subject matter of this disclosure.

Figure 2A:
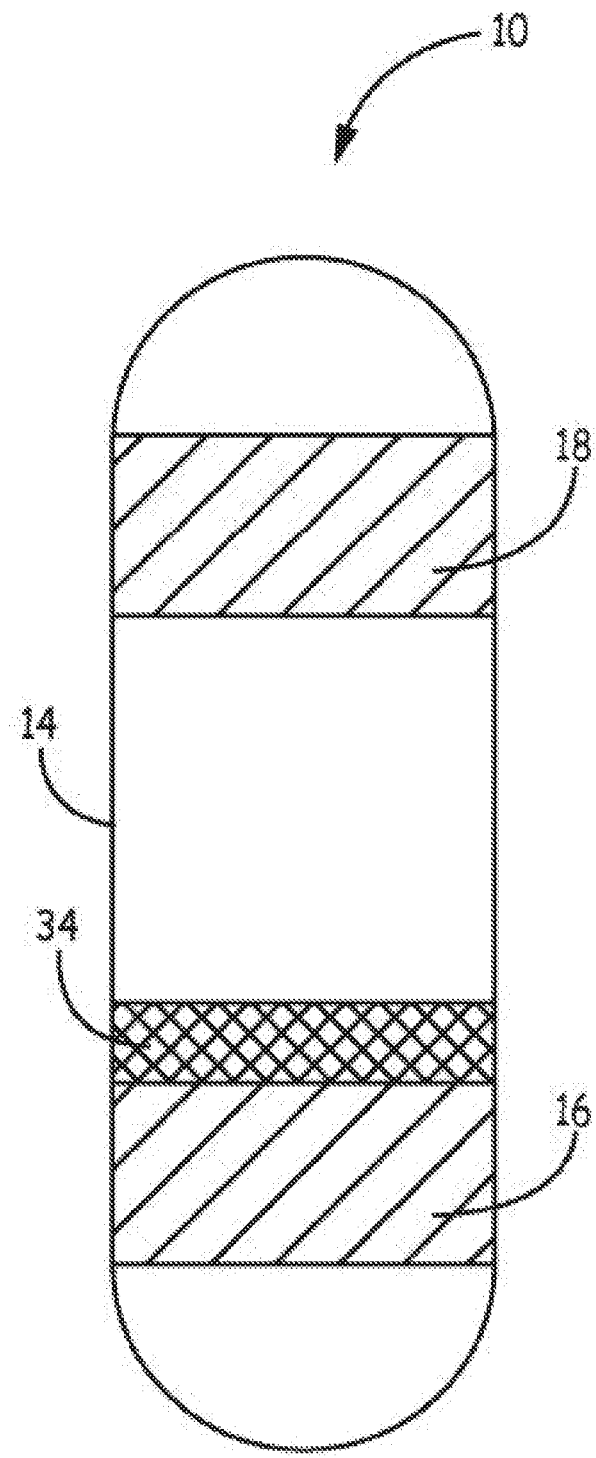
FIG. 2A is a conceptual view illustrating the leadless IPG of FIG. 1.

FIG. 2A is a conceptual view illustrating leadless IPG 10 of FIG. 1. As illustrated in FIG. 2A, leadless IPG 10 includes housing 14, electrodes 16 and 18, and a spacer 34. Housing 14 forms a hermetic seal that protects components of leadless IPG 10. As will be described in further detail herein, housing 14 may protect one or more processors, memories, transmitters, receivers, sensors, sensing circuitry, therapy circuitry, power sources, and other appropriate components.

Housing 14 may take on any of a number of shapes. In the example illustrated in FIG. 2A, housing 14 is generally cylindrical or pill-shaped. Housing 14 may have any of a number of shapes/dimensions. For example, housing 14 may be more of flat, rectangular shape. In one example, housing 14 may be less than approximately 30 mm in length and be less than or equal to 20 French. In other examples, housing 14 may be larger than 30 mm in length such that electrodes on the housing may be located over the atria and the ventricles.

Housing 14 of may be substantially formed of a conductive material, such as a medical grade stainless steel, titanium alloy, or other metal or metal alloy. Housing 14 also includes an insulative layer formed over at least a portion of housing 14, such as a layer of parylene, polyimide, or urethane. In some examples, electrodes 16 and 18 may be defined by uninsulated portions of an outward facing portion of housing 14. In some instances the insulative layer may be formed to focus, direct or point the electrodes toward heart 26. For example, the insulative layer may not extend around the full circumference of housing 14 to form an electrode 16 and/or 18 that only extends around a portion of the circumference of housing 14 (e.g., half, quarter or other portion). Housing 14 also includes a non-conductive spacer 34 that separates the portion of housing forming electrode 16 from the portion of housing forming electrode 18. Other division between insulated and uninsulated portions of housing 14 may be employed to define a different number or configuration of housing electrodes. In other instances, electrode 16 and/or 18 may be otherwise coupled to housing 14.

Electrodes 16 and 18 are illustrated in FIG. 2A as ring or cylindrical electrodes disposed on the exterior surface of housing 14. In one example, electrodes 16 and 18 may each have surface areas between approximately 2-55 mm$^2$. In another example, one or both of electrodes 16 and 18 may have surface areas up to 200 mm$^2$. Electrode 16 and electrode 18 may have an electrode spacing of between approximately 5-50 mm. Electrode 16 may be used as a cathode and electrode 18 may be used as an anode, or vice versa, for delivering electrical stimulation therapy to and/or sensing electrical signals associated with heart 26. In other examples, electrode 16 and/or 18 may be formed in other shapes, such as a hemispherical electrode that includes one of the ends of housing 14 or that does not extend around the entire circumference of housing 14.

Leadless IPG 10 may further include one or more anchoring mechanisms that are positioned along the length of the housing 14. The anchoring mechanisms may affix leadless IPG 10 to the loose connective tissue or other structures of the anterior mediastinum 28 to reduce movement of leadless IPG 10 from its desired location. The one or more anchoring mechanism(s) may either engage bone, fascia, muscle or other tissue of patient 12 or may simply be wedged therein to affix leadless IPG 10 under sternum 22 to prevent excessive motion or dislodgment.

Leadless IPGs of this disclosure may take on various other configurations. For example, a leadless IPG of this disclosure may conform with the leadless IPG illustrated and described in FIG. 2A and paragraphs [0040]-[0045] of copending U.S. Patent Application entitled, "IMPLANTABLE MEDICAL DEVICE SYSTEM HAVING IMPLANTABLE CARDIOVERTER-DEFIBRILLATOR (ICD) SYSTEM AND SUBSTERNAL LEADLESS PACING DEVICE" (U.S. Pat. No. 9,717,923) filed on Apr. 25, 2014. The entire content of the referenced portions are incorporated herein by reference in their entirety.

Figure 2B:
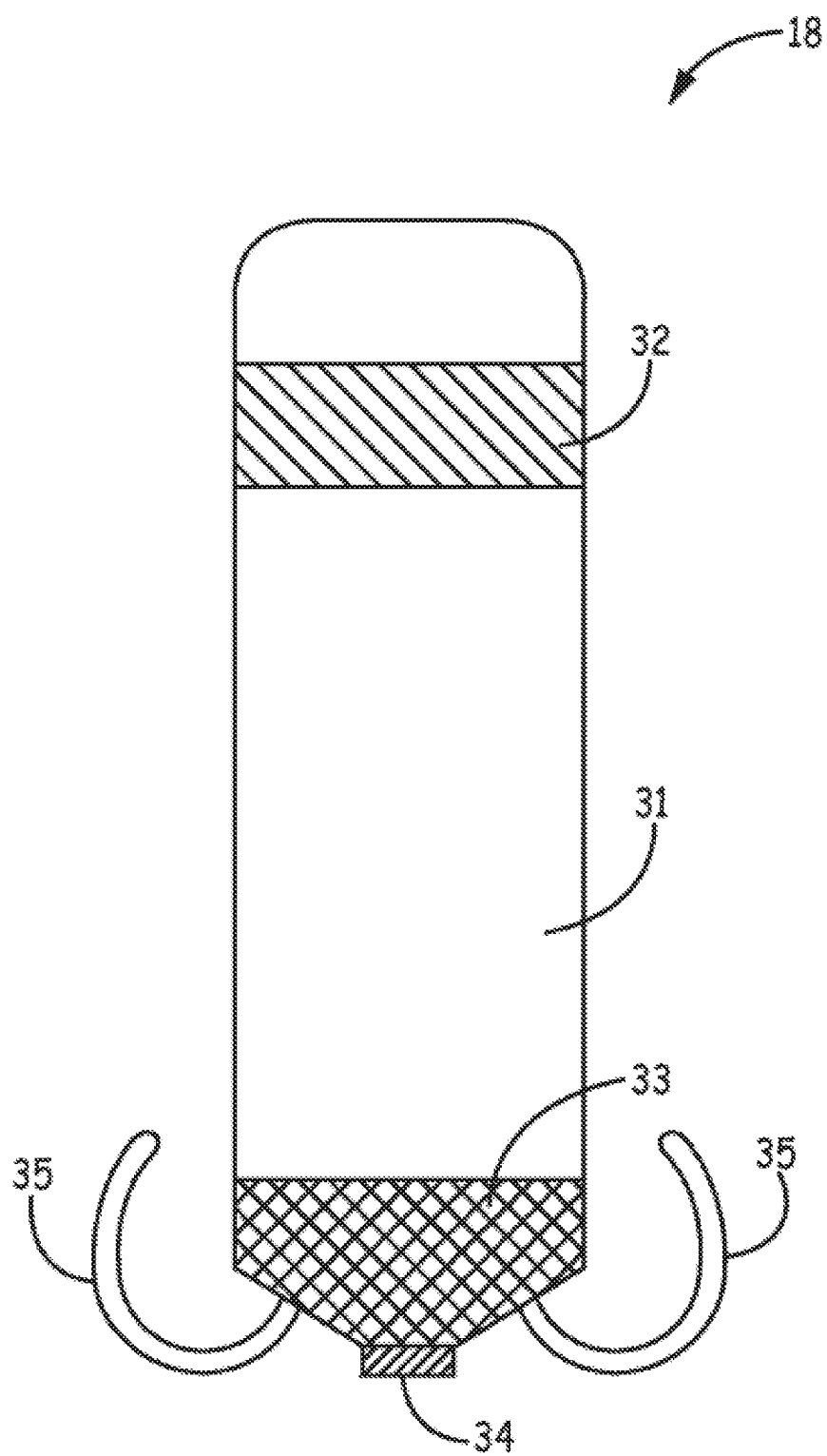
FIG. 2B illustrates a conceptual view of an example leadless implantable pulse generator in further detail.

An example leadless IPG 18 is illustrated in further detail in FIG. 2B. As illustrated in FIG. 2B, leadless IPG 18 includes a housing 31, electrodes 32 and 34 coupled to housing 31 or formed by housing 31, a non-conductive spacer 33 and a fixation mechanism (e.g., tines 35 of FIG. 2B) to attach leadless IPG 18 at a desired location within anterior mediastinum 36. Leadless IPG 18 may have other fixation mechanisms in addition to or instead of tines 35.

Housing 31 forms a hermetic seal that protects components of leadless IPG 18. As will be described in further detail herein, housing 31 may protect one or more processors, memories, transmitters, receivers, sensors, sensing circuitry, therapy circuitry, power sources, and other appropriate components. Housing 31 may take on any of a number of shapes. In the example illustrated in FIG. 2B, housing 31 is generally cylindrical or pill-shaped. In another example, housing 14 may be more of flat, rectangular shape. Housing 31 may have any of a number of dimensions. In one example, housing 31 may be less than approximately 30 mm in length and be less than or equal to 20 French. In other examples, housing 14 may be larger than 30 mm in length such that electrodes on the housing may be located over both the atria and the ventricles.

Housing 31 of may be substantially formed of a conductive material, such as a medical grade stainless steel, titanium alloy, or other metal or metal alloy. Housing 31 also includes an insulative layer formed over at least a portion of housing 31, such as a layer of parylene, polyimide, or urethane. In some examples, electrodes 32 and 34 may be defined by uninsulated portions of an outward facing portion of housing 31. Housing 31 also includes a non-conductive spacer 33 that separates the portion of housing forming electrode 32 from the portion of housing forming electrode 34. Other division between insulated and uninsulated portions of housing 31 may be employed to define a different number or configuration of housing electrodes. In other instances, electrode 32 and/or 34 may be otherwise coupled to housing 31.

Electrodes 32 and 34 are illustrated in FIG. 2B as a tip electrode and ring or cylindrical electrode, respectively, disposed on the exterior surface of housing 31. In one example, electrodes 32 and 34 may each have surface areas between approximately 2-55 $mm^2$. In another example, one or both of electrodes 16 and 18 may have surface areas up to 200 $mm^2$. Electrode 32 and electrode 34 may have an electrode spacing of between approximately 5-30 mm. In other instances, such as when multi-chamber sensing or pacing is desired, housing 31 may be much longer, e.g., up to 20 or 30 cm, and the electrode spacing may be up to 16 cm. Electrode 32 may be used as a cathode and electrode 34 may be used as an anode, or vice versa, for delivering electrical stimulation therapy to and/or sensing electrical signals associated with heart 26. In other examples, electrode 32 and/or 34 may be formed in other shapes, such as a hemispherical electrode that includes one of the ends of housing 31 or that does not extend around the entire circumference of housing 31.

In some instances, electrodes 32 and 34 or housing 31 of leadless IPG 18 may be shaped, oriented, designed or otherwise configured to reduce extra-cardiac stimulation. For example, electrodes 32 and 34 or housing 31 may be shaped, oriented, designed or otherwise configured to focus, direct or point electrodes 32 and 34 toward heart 26. In this manner, pacing pulses delivered by leadless IPG 18 are directed toward heart 26 and not outward toward skeletal muscle. For example, electrodes 32 or 34 or housing 31 may be partially coated or masked with a polymer (e.g., polyurethane) or another coating material (e.g., tantalum pentoxide) on one side or in different regions so as to direct the pacing signal toward heart 26 and not outward toward skeletal muscle.

Leadless IPG 18 of this disclosure may take on various other configurations. For example, leadless IPG 18 of this disclosure may conform with the leadless IPG illustrated and described in FIG. 2B.

Leadless IPG 18 may analyze the sensed electrical signals of heart 26 obtained from electrodes 32 and 34 to detect cardiac events, e.g., tachycardia. Leadless IPG 18 also provides pacing pulses to heart 26 via electrodes 32 and 34. Leadless IPG 18 may be configured to generate and deliver the pacing pulses to provide anti-tachycardia pacing (ATP), bradycardia pacing, post shock pacing, or other pacing therapies or combination of pacing therapies. In one example, leadless IPG 18 may generate and deliver ATP therapy in response to detecting ventricular tachycardia. In another example, leadless IPG 18 may generate and deliver ATP therapy in response to receiving a communication from ICD 14 indicating that ICD 14 detected ventricular tachycardia. In another example, leadless IPG 18 may detect delivery of a defibrillation or cardioversion shock and provide post-shock pacing in response to detecting delivery of the shock. In this manner, ATP therapy (or other pacing therapy) may be provided in a subcutaneous ICD system without entering the vasculature or the pericardium.

Figure 3A:
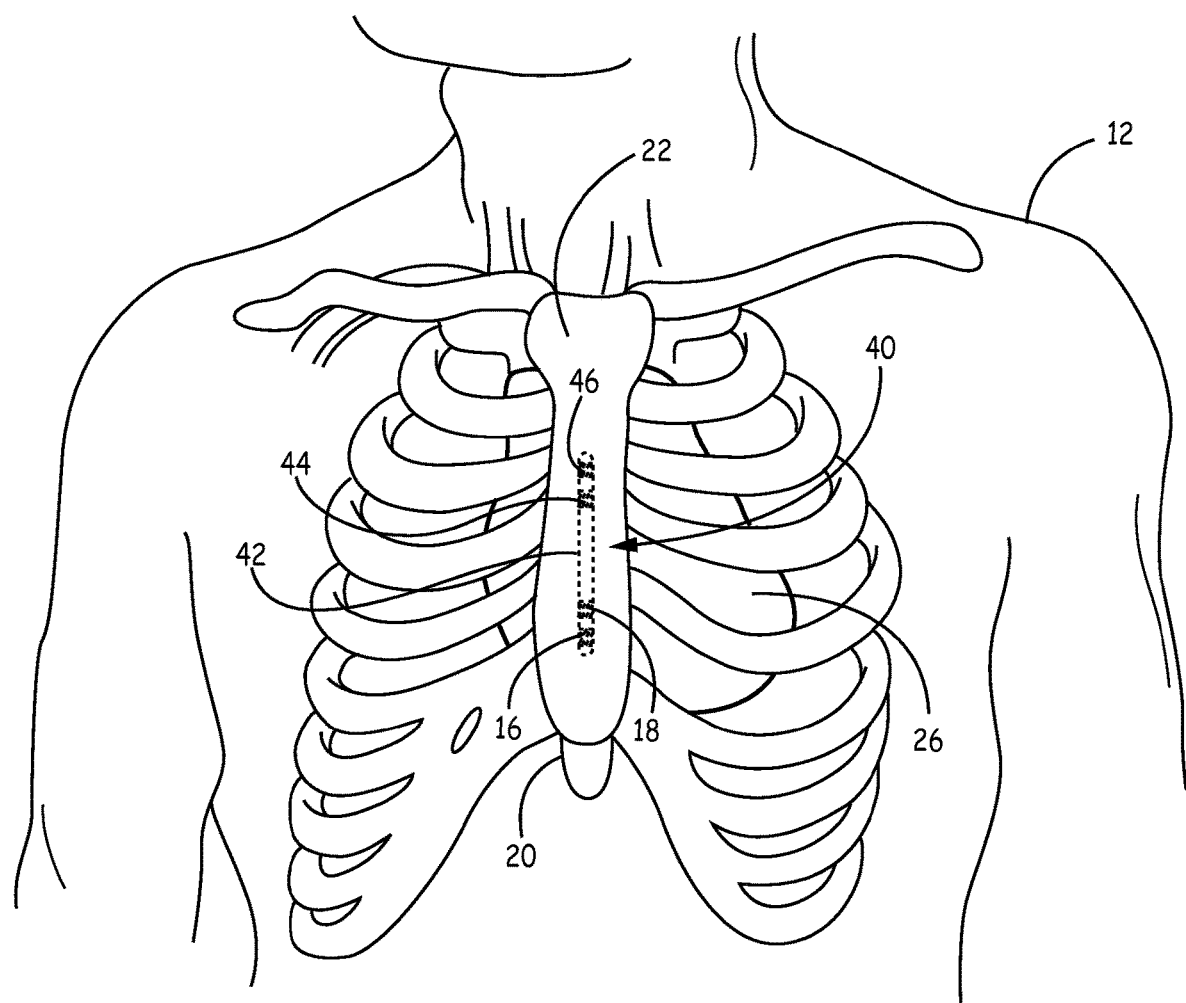
FIG. 3A is a front view of another example leadless IPG implanted within a patient.
Figure 3B:
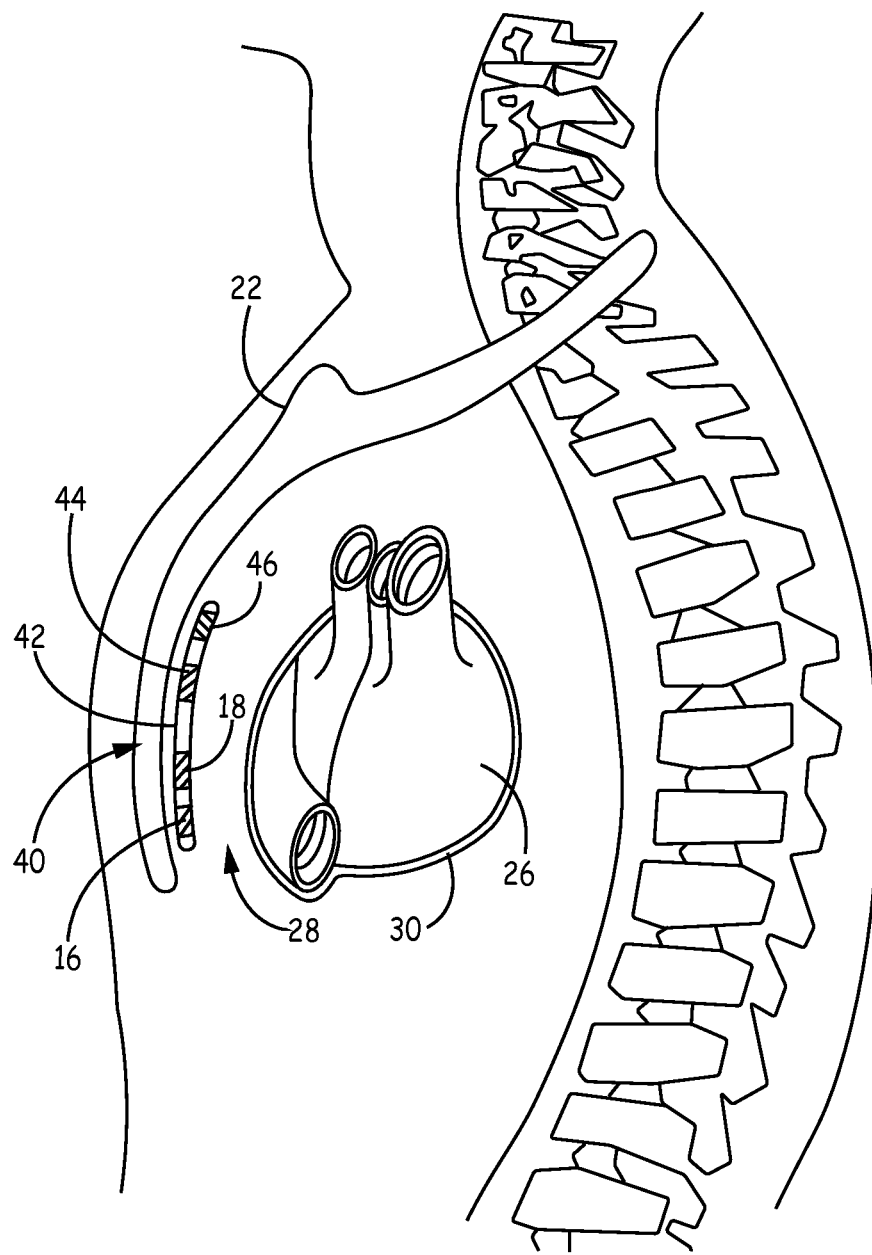
FIG. 3B is a side view of the leadless IPG of FIG. 3A implanted within the patient.

FIGS. 3A and 3B are conceptual diagrams of another example leadless IPG 40 implanted within patient 12. FIG. 3A is a front view of patient 12 implanted with leadless IPG 40. FIG. 3B is a side view of patient 12 with leadless IPG 40. Leadless IPG 40 conforms substantially to implantable cardiac leadless IPG 10 of FIGS. 1A-1C, but housing 42 of leadless IPG 40 electrodes 44 and 46 in addition to electrodes 16 and 18. Repetitive description of like numbered elements described in other embodiments is omitted for sake of brevity.

Housing 42 conforms substantially to housing 14 of leadless IPG 10. Thus, housing 42 may include the structure and/or function described above with respect to housing 14.

Housing 42 may, however, have a length that is longer than housing 14 of leadless IPG 10 to enable a first portion of housing 42 including electrodes 44 and 46 to be implanted over an atrium of heart 26 and a second portion of housing 42 including electrodes 16 and 18 to be implanted over a ventricle of heart 26 (e.g., as viewed via an AP fluoroscopic view of heart 26).

Electrodes 44 and 46 conform substantially to electrodes 16 and 18. Therefore, description of electrodes 16 and 18 will not be repeated here, but is equally applicable to electrodes 44 and 46. Housing 42 may also include additional non-conductive spacers (not shown) to isolate electrodes 44 and 46 from one another and to isolate electrodes 44 and 46 from electrodes 16 and 18. In other embodiments, housing 42 may include more or fewer electrodes. For example, housing 42 may include only two electrodes with the first electrode being placed near the atria of the heart to sense and/or pace the atrium and the second electrode being placed near the ventricle of the heart to sense and/or pace the ventricle. In this manner, leadless IPG 40 may provide multi-chamber sensing and/or pacing.

Figure 4A:
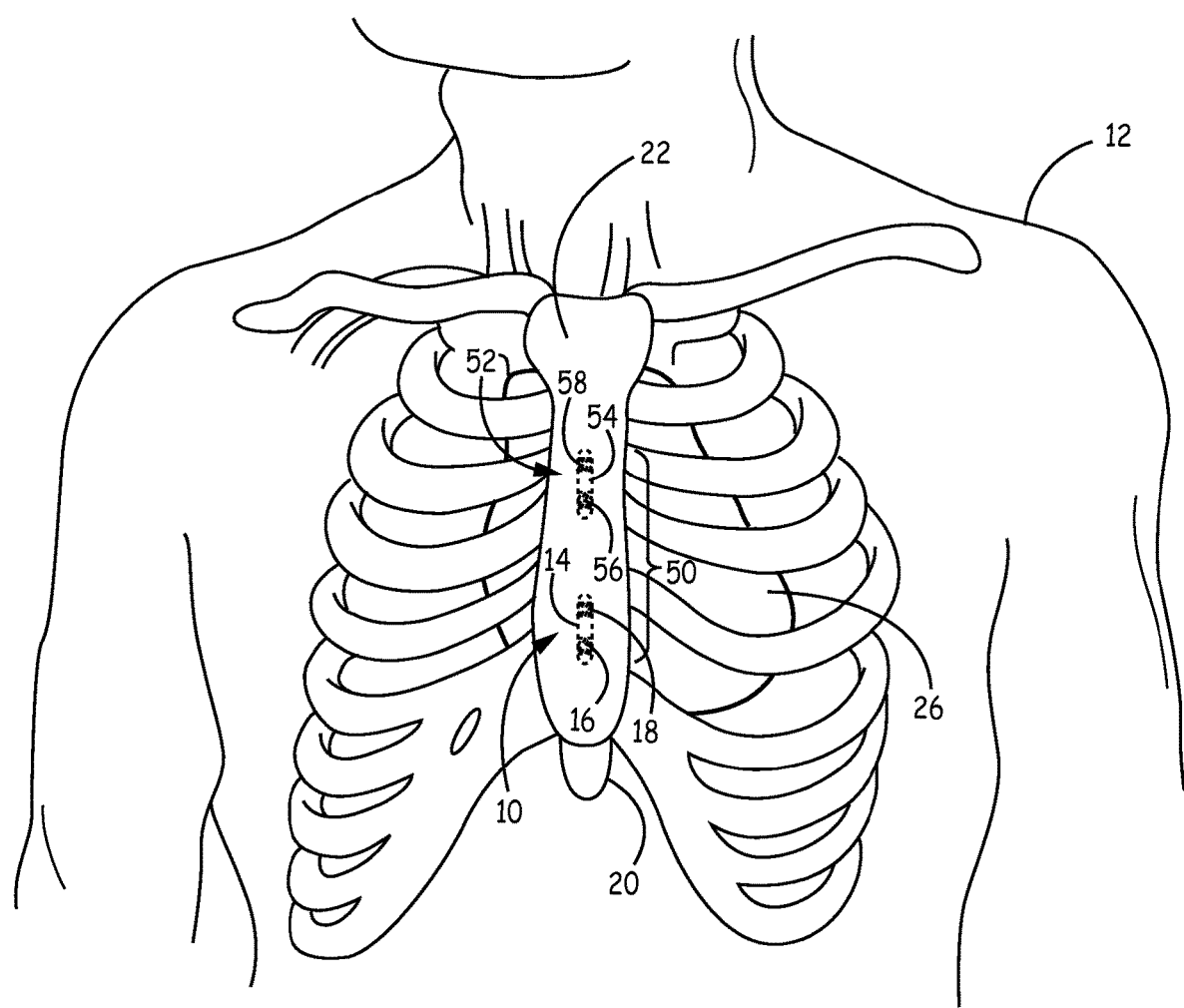
FIG. 4A is a front view of a further example leadless IPG implanted within a patient.
Figure 4B:
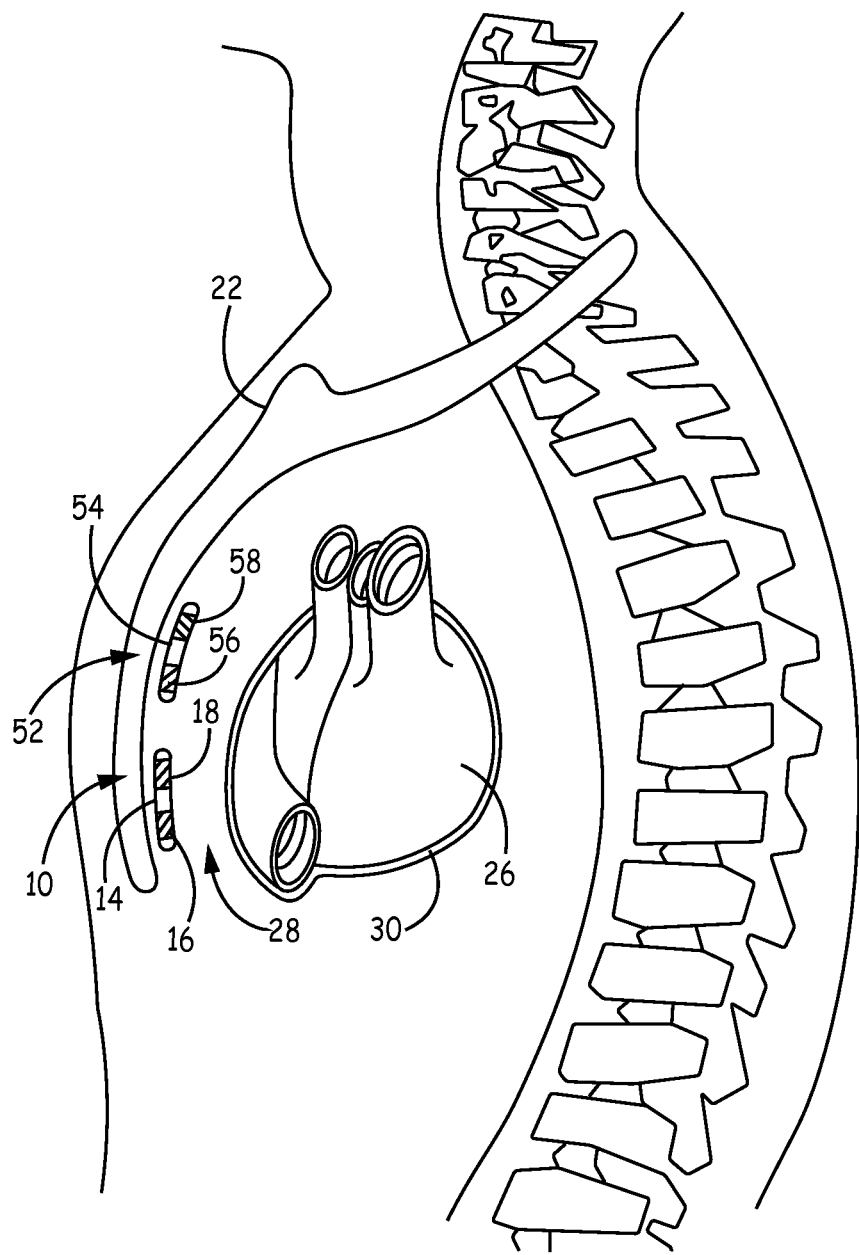
FIG. 4B is a side view of the leadless IPG of FIG. 4A implanted within the patient.

FIGS. 4A and 4B are conceptual diagrams of an example cardiac stimulation system 50 that includes multiple leadless IPGs implanted within patient 12. FIG. 4A is a front view of patient 12 implanted with implantable cardiac stimulation system 50. FIG. 4B is a side view of patient 12 with implantable cardiac stimulation system 50. Repetitive description of like numbered elements described in other embodiments is omitted for sake of brevity.

Cardiac stimulation system 50 includes a first leadless IPG 10 and a second leadless IPG 52. Leadless IPG 10 is described above in detail with respect to FIGS. 1A-1C. Leadless IPG 52 (e.g., housing 54 and electrodes 56 and 58) conforms substantially to leadless IPG 10 (e.g., housing 14 and electrodes 16 and 18). As such, the structure and/or function described above with respect to leadless IPG 10, housing 14, and electrodes 16 and 18 are equally applicable to leadless IPG 52, housing 54, and electrodes 56 and 58.

Leadless IPG 52 is implanted substantially within anterior mediastinum 28 such that leadless IPG 52 can sense electrical activity of the atria of heart 26 and/or deliver electrical stimulation to the atria of heart 26 via electrodes 56 and 58. In one example, leadless IPG 52 may be implanted such that electrodes 56 and 58 are located substantially over a cardiac silhouette of one or both atria as observed via an AP fluoroscopic view of heart 26. In another example, leadless IPG 52 may be implanted such that a bipolar therapy or sense vector between electrodes 56 and 58 is centered or otherwise located over the atrium. However, leadless IPG 52 may be positioned at other locations as long as the bipolar therapy vector between electrodes 56 and 58 result in capture of the atrium of heart 26. In this manner, cardiac stimulation system 50 may provide multi-chamber pacing. In another example, leadless IPG 52 may be a sensing-only device.

In some instances, leadless IPG 10 and leadless IPG 52 may operate independently of one another. In other instances, leadless IPG 10 and leadless IPG 52 may coordinate delivery of stimulation therapy by communicating with one another either via one-way or two-way communication.

Figure 5:
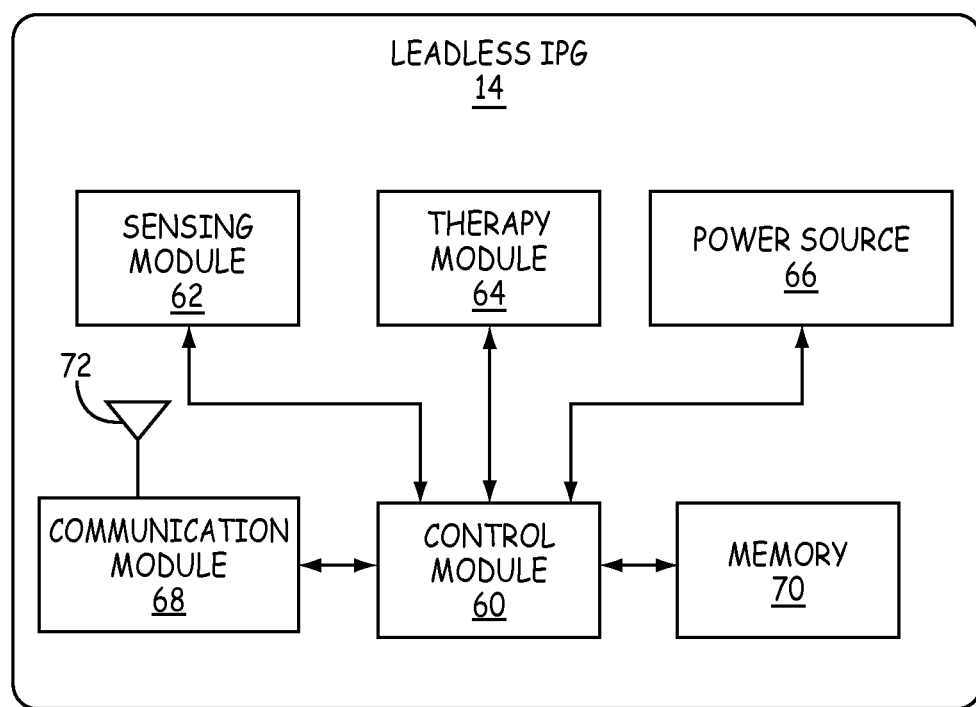
FIG. 5 is a functional block diagram of an example configuration of electronic components of an example leadless IPG.

FIG. 5 is a functional block diagram of an example configuration of electronic components of an example leadless IPG 10. However, the discussion below is equally applicable to leadless IPG 40 and 52. Leadless IPG 10 includes a control module 60, sensing module 62, therapy module 64, communication module 68, and memory 70. The electronic components may receive power from a power source 66, which may be a rechargeable or non-rechargeable battery. In other embodiments, leadless IPG 10 may include more or fewer electronic components. The described modules may be implemented together on a common hardware component or separately as discrete but interoperable hardware, firmware, or software components. Depiction of different features as modules is intended to highlight different functional aspects and does not necessarily imply that such modules must be realized by separate hardware, firmware, or software components. Rather, functionality associated with one or more modules may be performed by separate hardware, firmware, or software components, or integrated within common or separate hardware or software components.

Sensing module 62 is electrically coupled to electrodes 16 and 18 via conductors internal to housing 14 of leadless IPG 10. Sensing module 62 is configured to obtain signals sensed via one or more sensing vectors formed by electrodes 16 and 18, and the housing electrode of leadless IPG 10 and process the obtained signals.

The components of sensing module 62 may be analog components, digital components or a combination thereof. Sensing module 62 may, for example, include one or more sense amplifiers, filters, rectifiers, threshold detectors, analog-to-digital converters (ADCs) or the like. Sensing module 62 may convert the sensed signals to digital form and provide the digital signals to control module 60 for processing or analysis. For example, sensing module 62 may amplify signals from the sensing electrodes and convert the amplified signals to multi-bit digital signals by an ADC. Sensing module 62 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to control module 60.

Control module 60 may process the signals from sensing module 62 to monitor electrical activity of heart 26 of patient 12. Control module 60 may store signals obtained by sensing module 62 as well as any generated EGM waveforms, marker channel data or other data derived based on the sensed signals in memory 70. Control module 60 may analyze the EGM waveforms and/or marker channel data to deliver pacing pulses based on the sensed cardiac events, e.g., pacing pulses triggered or inhibited based on the detection or lack of detection of intrinsic cardiac activity. In some instances, control module 60 may also detect cardiac events, such as tachyarrhythmia, based on the sensed electrical signals.

Therapy module 64 is configured to generate and deliver electrical stimulation therapy to heart 26. Therapy module 64 may include one or more pulse generators, capacitors, and/or other components capable of generating and/or storing energy to deliver as pacing therapy. Control module 60 may control therapy module 64 to generate electrical stimulation therapy and deliver the generated therapy to heart 26 via one or more therapy vectors formed by electrodes 16 and 18 and the housing electrode of leadless IPG 10 according to one or more therapy programs, which may be stored in memory 70. Control module 60 controls therapy module 64 to generate electrical stimulation therapy with the amplitudes, pulse widths, timing, and frequencies specified by a selected therapy program.

In some instances, control module 60 may control therapy module 64 to deliver the pacing therapy based on the electrical signals sensed via the sensing vector between electrode 16 and 18. Thus, control module 60 may control therapy module 64 to deliver pacing therapy using pacing modes such as AAI or VVI in instances in which leadless IPG 10 is utilized or in modes such as AAI, VVI, DDD, DDI, VAT, VDD, or DVI in instances in which leadless IPG 40 or cardiac stimulation system 50 are utilized. In other instances, control module 60 may control therapy module 64 to deliver pacing pulses independent of sensing, e.g., using asynchronous pacing modes such as AOO, VOO, DOO, or other mode with no sensing or with no inhibiting or triggering in response to sensing, e.g., AAO, VVO, or the like. Control module 60 may control therapy module 64 to further provide pacing that is rate-responsive in addition to any of the modes described above.

Therapy module 64 may generate and deliver pacing pulses with any of a number of amplitudes, pulse widths, or other characteristic to capture heart 26. For example, the pacing pulses may be monophasic, biphasic, or multi-phasic (e.g., more than two phases). The pacing thresholds of heart 26 when delivering pacing pulses from anterior mediastinum 36 may depend upon a number of factors, including location, type, size, orientation, and/or spacing of the electrodes, physical abnormalities of heart 26 (e.g., pericardial adhesions or myocardial infarctions), or other factor(s).

The increased distance from electrodes 16 and 18 to the heart tissue may result in heart 26 having increased pacing thresholds compared to transvenous pacing thresholds. To this end, therapy module 64 may be configured to generate and deliver pacing pulses having larger amplitudes and/or pulse widths than conventionally required to obtain capture via transvenously implanted lead or a lead attached to heart 26. In one example, therapy module 64 may generate and deliver pacing pulses having amplitudes of less than or equal to 8 volts and pulse widths between 0.5-3.0 milliseconds. In another example, therapy module 64 may generate and deliver pacing pulses having amplitudes of between 5 and 10 volts and pulse widths between approximately 3.0 milliseconds and 10.0 milliseconds. In another example, pulse widths of the pacing pulses may be between approximately 2.0 milliseconds and 8.0 milliseconds. In a further example, therapy module 64 may generate and deliver pacing pluses having pulse widths between approximately 0.5 milliseconds and 20.0 milliseconds. In another example, therapy module 64 may generate and deliver pacing pluses having pulse widths between approximately 1.5 milliseconds and 20.0 milliseconds.

In some cases, therapy module 64 may generate pacing pulses having longer pulse durations than conventional transvenous pacing pulses to achieve lower energy consumption. For example, therapy module 64 may be configured to generate and deliver pacing pulses having pulse widths or durations of greater than two (2) milliseconds. In another example, therapy module 64 may be configured to generate and deliver pacing pulses having pulse widths or durations of between greater than two (2) milliseconds and less than or equal to three (3) milliseconds. In another example, therapy module 64 may be configured to generate and deliver pacing pulses having pulse widths or durations of greater than or equal to three (3) milliseconds. In another example, therapy module 64 may be configured to generate and deliver pacing pulses having pulse widths or durations of greater than or equal to five (5) milliseconds. In another example, therapy module 64 may be configured to generate and deliver pacing pulses having pulse widths or durations of greater than or equal to ten (10) milliseconds. In a further example, therapy module 64 may be configured to generate and deliver pacing pulses having pulse widths between approximately 3-10 milliseconds. In a further example, therapy module 64 may be configured to generate and deliver pacing pulses having pulse widths or durations of greater than or equal to fifteen (15) milliseconds. In yet another example, therapy module 64 may be configured to generate and deliver pacing pulses having pulse widths or durations of greater than or equal to twenty (20) milliseconds.

Depending on the pulse widths, therapy module 64 may be configured to generate and deliver pacing pulses having pulse amplitudes less than or equal to twenty (20) volts, deliver pacing pulses having pulse amplitudes less than or equal to ten (10) volts, deliver pacing pulses having pulse amplitudes less than or equal to five (5) volts, deliver pacing pulses having pulse amplitudes less than or equal to two and one-half (2.5) volts, deliver pacing pulses having pulse amplitudes less than or equal to one (1) volt. In other examples, the pacing pulse amplitudes may be greater than 20 volts. These pulse amplitudes may be combined with any of the pulse widths/durations described above. Reducing the amplitude of pacing pulses delivered by leadless IPG 10 may reduce the likelihood of extra-cardiac stimulation. Some experimental results are provided later illustrating some example combinations of pacing amplitudes and widths obtained using pacing leads.

Communication module 68 includes any suitable hardware, firmware, software or any combination thereof for communicating with another device, such as a clinician programmer, a patient monitoring device, or the like. For example, communication module 68 may include appropriate modulation, demodulation, frequency conversion, filtering, and amplifier components for transmission and reception of data with the aid of antenna 72. Communication module 68 may communicate with an external device, e.g., an external programmer, to obtain operating parameters or provide sensed data for analysis or review. In another example, communication module 68 may be configured to communicate with another leadless IPG to coordinate delivery of pacing pulses to the atrium and/or ventricle as described with respect to FIG. 4. Communication module may communicate using any of a number of techniques including inductive communication, magnetic communication, electromagnetic communication (e.g., RF), optical communication, tissue conductance communication, or the like.

The various modules of leadless IPG 10 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 70 may include computer-readable instructions that, when executed by control module 60 or other component of leadless IPG 10, cause one or more components of leadless IPG 10 to perform various functions attributed to those components in this disclosure. Memory 70 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

Experiments

Three acute procedures were performed using pigs, with the animals in a dorsal recumbency. An incision was made near the xiphoid process and a Model 4194 lead was delivered to the substernal/retrosternal space using a 6996T tunneling tool and sheath. An active can emulator (ACE)

was placed in a subcutaneous pocket on either the right chest (first acute experiment) or the left midaxillary (second and third acute experiments). Various pacing configurations were tried and different pieces of equipment were used as the source of stimulation. Multiple pulse widths were used in delivering the pacing pulse. Across experiments, several different substernal/retrosternal lead electrode locations were utilized.

In the second and third experiments the impact of lead location on electrical performance was investigated by moving the lead to several locations under the sternum and collecting data to generate strength-duration curves at each location.

In all three acute experiments, the substernal/retrosternal lead was placed and electrical data collected. The lead was moved intentionally many times across experiments to better understand the location best suited to capturing the heart at low pacing thresholds, with different locations and parameters tried until pacing capability was gained and lost. A range of thresholds based on location and pacing configuration was recorded. For this reason, the lowest threshold result for each acute experiment is reported, as are strength-duration curves showing the range of pacing values obtained from suitable pacing locations. In all cases, it was determined that positioning the substernal/retrosternal pacing electrode approximately over the ventricle of the cardiac silhouette provided best results.

Experiment 1

In the first acute study, a MEDTRONIC ATTAIN bipolar OTW 4194 lead (referred to herein as "the 4194 lead") was implanted substernally, and two active can emulators were positioned, one in the right dorsal lateral region (ACE1) and one on the right midaxillary (ACE2). The 4194 lead was placed directly below the sternum, in the mediastinum, with the lead tip and body running parallel to the length of the sternum. Various pacing configurations were tried and electrical data collected.

The smallest threshold observed was 0.8 volts, obtained when pacing from the tip of the substernal/retrosternal 4194 lead to ACE1 (10 ms pulse width and Frederick Heir instrument as the source of stimulation). It was possible to capture using a smaller pulse width, though threshold increased as the pulse width shortened (1.5V at 2 ms in this same configuration with the Frederick Heir Stimulator. Many additional low thresholds (1-2 volts) were obtained with different pacing configurations and pulse durations.

Figure 6:
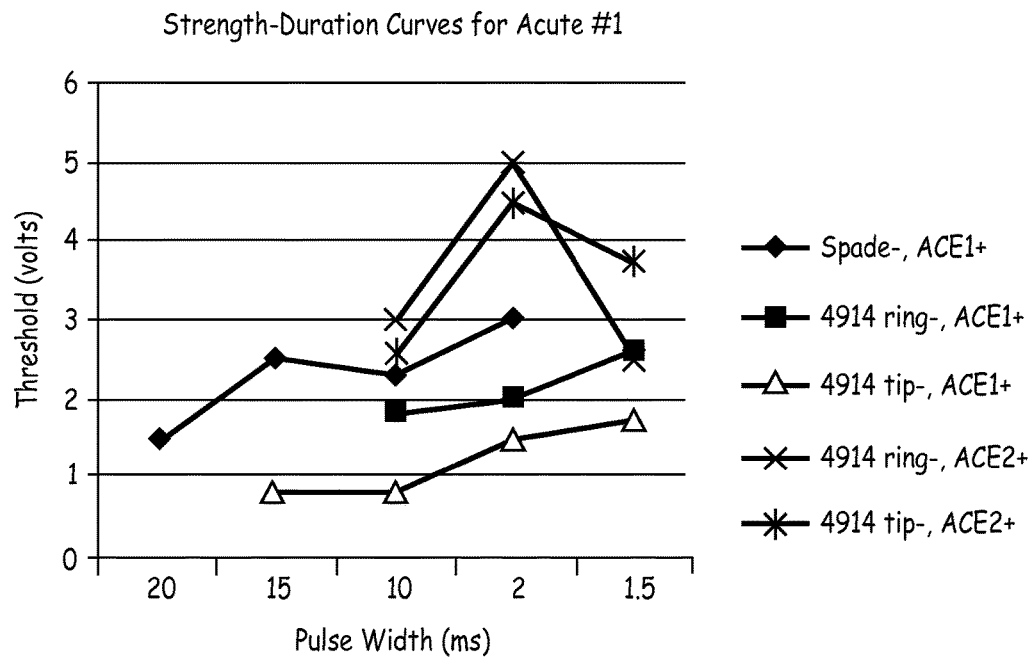
FIG. 6 is a graph illustrating strength-duration curves showing the capture thresholds obtained at various pulse widths during a first acute study.

FIG. 6 illustrates a strength-duration curve showing the capture thresholds obtained at various pulse widths during the first acute study. Note that all configurations paced from either the tip or the ring of the substernally implanted 4194 lead (−) to one of the two active can emulators (+). In one instance, a large spade electrode (instead of a Model 4194 lead) was used as the substernal/retrosternal electrode, as noted in the legend of.

As shown, several pacing configurations and parameters were tried. Across the configurations reported in the graph above, threshold values ranged from 0.8 volts to 5.0 volts, with threshold generally increasing as pulse width was shortened. In a few instances, the threshold at 1.5 ms pulse width was smaller than the threshold at 2.0 ms. It should be noted that the threshold value obtained at 1.5 ms was always recorded using the Medtronic 2290 analyzer as the stimulation source, whereas all other threshold measurements for the first acute experiment (at pulse widths of 2, 10, 15 and 20 ms) were obtained using a Frederick Heir instrument as the source of stimulation. Differences in these two instruments may account for the difference in threshold values at similar pulse widths (1.5 ms and 2 ms).

In general, the first acute experiment demonstrated the feasibility of substernal/retrosternal pacing by producing small capture thresholds (average=2.5±1.2 volts), using several different pacing configurations and parameters.

Experiment 2

A second acute experiment was conducted. In the second acute, however, the animal presented with pericardial adhesions to the sternum. Because of the pericardial adhesion, the ventricular surface of the cardiac silhouette was rotated away from the sternum—an anatomical difference that may have resulted in higher thresholds throughout this experiment.

As in the previous acute experiment, a Model 4194 lead was placed under the sternum. An active can emulator was placed on the left midaxillary. The tip to ring section of the 4194 was positioned over the cardiac silhouette of the ventricle, as observed by fluoroscopy, and this position is notated "Position A" on the strength-duration graph illustrated in FIG. 7. The lead eventually migrated a very short distance closer to the xiphoid process during stimulation (still under the sternum) to reach "Position B," and additional electrical measurements were obtained successfully from this position as well.

The smallest threshold observed in the second acute experiment was 7V, obtained when pacing from the substernal/retrosternal 4194 ring electrode (−) to an ACE (+) on the left midaxillary in the first lead position (5 ms, 15 ms and 20 ms pulse widths, Frederick Heir stimulator). Additionally, thresholds of 8 and 9 volts were obtained with the lead in the second anatomical position, both from 4194 tip to ACE (unipolar) and 4194 tip to ring (bipolar) configurations at multiple pulse widths. The two lines that appear to run off the chart were instances of no capture.

Figure 7:
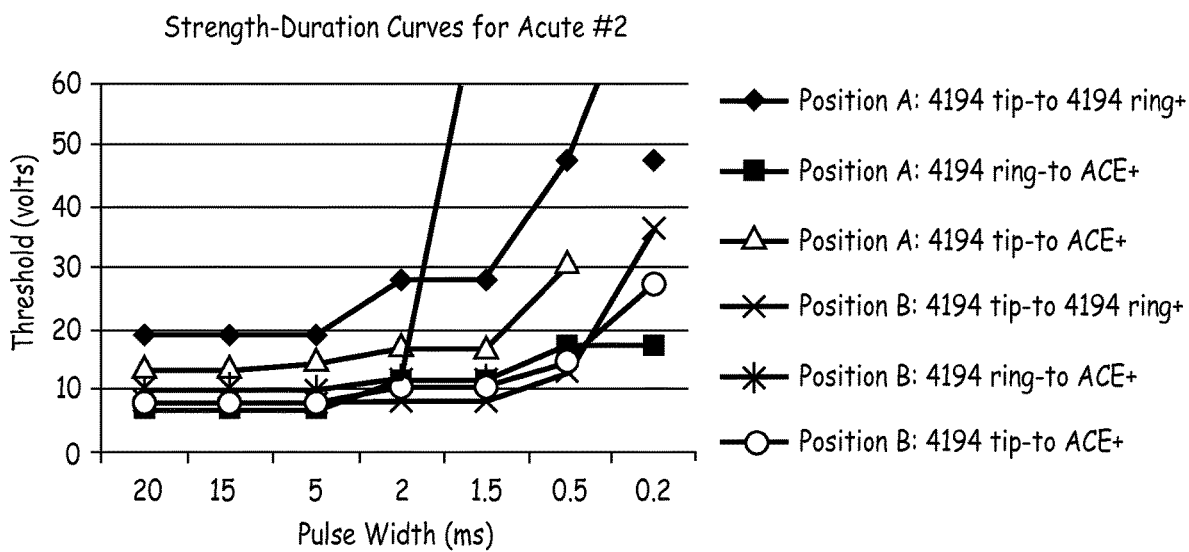
FIG. 7 is a graph illustrating strength-duration curves showing the capture thresholds obtained at various pulse widths during a second acute study.

All of the electrical values reported in FIG. 7 were collected with the Frederick Heir instrument as the stimulation source. Extra-cardiac stimulation was observed with many of the electrical measurements obtained in a unipolar pacing configuration. No obvious extra-cardiac stimulation was observed when pacing in a bipolar configuration (4194 tip to ring), though a low level of stimulation could be felt with a hand on the animal's chest.

Experiment 3

A third and final acute experiment was conducted demonstrating the feasibility of substernal/retrosternal pacing. As in the previous two acute experiments, a 4194 lead was placed under the sternum. An active can emulator was placed on the left midaxillary. In this experiment, the substernal/retrosternal 4194 lead was intentionally positioned so that the lead tip was initially near the second rib, far above the cardiac silhouette of the ventricle. The lead tip was then pulled back (toward the xiphoid process) one rib space at a time, collecting electrical data at each position. As in previous experiments, low capture thresholds were obtained when the pacing electrodes were approximately positioned over the ventricular surface of the cardiac silhouette, as observed via fluoroscopy. When the lead tip was not over the ventricular surface of the cardiac silhouette, "no capture" was often the result.

As in previous experiments, pacing was performed from either the tip or the ring of the substernal/retrosternal 4194 lead (−) to the ACE (+) on the left midaxillary. However, in this acute experiment, a subcutaneous ICD lead was also positioned in its subcutaneous arrangement (as illustrated and described in FIGS. 1A-C). In some instances, the pacing configuration was from either the tip or the ring of the substernal/retrosternal 4194 lead (−) to either the ring or the coil of the subcutaneous ICD lead (+), so that the ICD lead and not the ACE was the indifferent electrode.

The smallest threshold observed across the experiment was 0.8V, obtained when pacing from the substernal/retrosternal 4194 tip electrode (−) to an ACE (+) on the left midaxillary when the lead was positioned such that the lead tip electrode was approximately under the sixth rib (20 ms pulse width and Frederick Heir stimulator). Many additional low thresholds were obtained with different pacing configurations, shorter pulse durations and different lead positions, again demonstrating the feasibility of substernal/retrosternal pacing. Obvious extra-cardiac stimulation generally was not observed with lower threshold measurements (at longer pulse durations) but was observed at higher thresholds.

The strength duration curves for lead positions 3-5 are presented in FIGS. 5-7, with individual graphs for each location due to the breadth of electrical data collected. Measurements made with the 2290 analyzer as the source of stimulation are noted. Other electrical measurements were made with the Frederick Heir instrument as the stimulation source.

Figure 8:
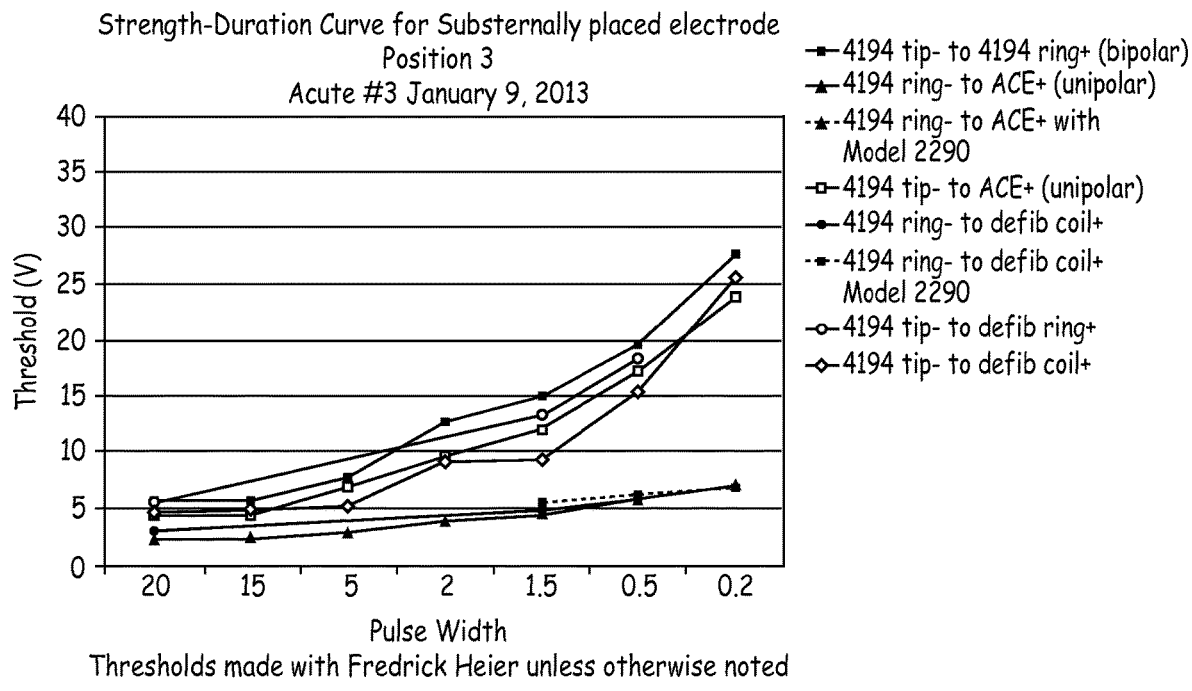
FIG. 8 is a graph illustrating strength-duration curves of electrical data from a third acute experiment.

FIG. 8 illustrates the strength-duration curve of electrical data from the third acute experiment when the 4194 lead tip was positioned under the sternum at the location of the $4^{th}$ rib. Several therapy vectors resulted in low pacing thresholds, generally when pulse widths were quite long. At shorter pulse widths, threshold increased.

Figure 9:
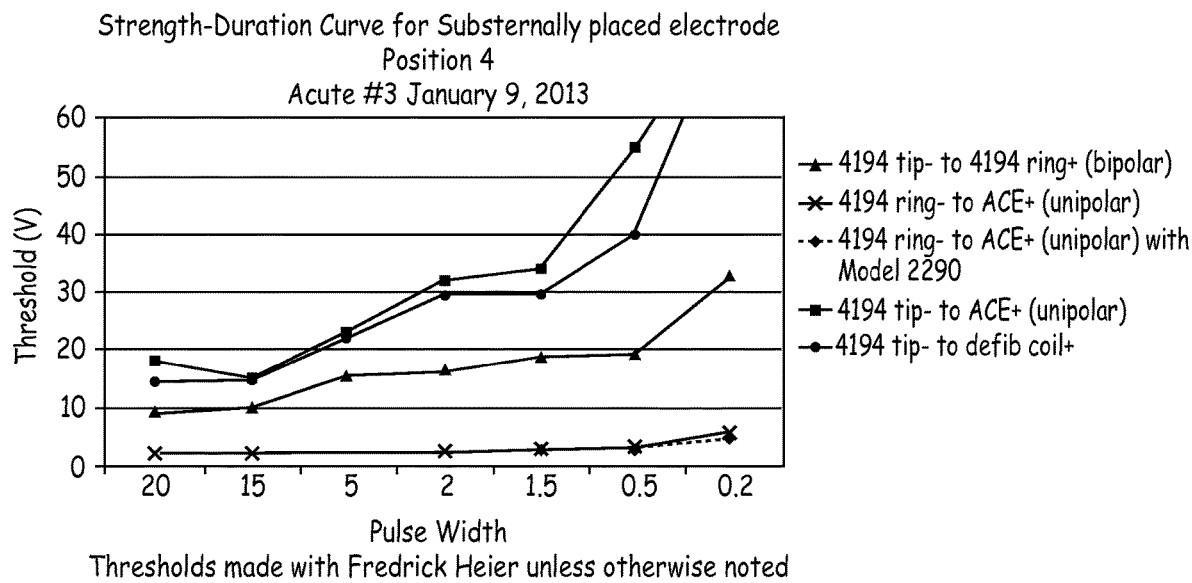
FIG. 9 is a graph illustrating strength-duration curves of electrical data from the third acute experiment.

FIG. 9 illustrates the strength-duration curve of electrical data from the third acute experiment when the 4194 lead tip was positioned under the sternum at the location of the $5^{th}$ rib. The two lines that appear to run off the chart at 0.2 ms were instances of no capture. FIG. 9 demonstrates the position dependence of the substernal/retrosternal lead. Thresholds were higher overall in this anatomical location (the lead tip near the $5^{th}$ rib), though capture was still possible and in the 4194 ring (−) to ACE (+) configuration, moderately low (2 volts at 20 ms). There generally was no significant extra-cardiac stimulation observed except with pulse widths of 0.2 ms and 0.5 ms in the 4194 tip (−) to ACE (+) configuration and in the unipolar configuration going from the 4194 tip (−) to the coil of the subcutaneous ICD lead at pulse widths of 1.5 ms and shorter, all of which resulted in the highest recorded threshold readings in this lead position.

FIG. 10 illustrates the strength-duration curve of electrical data from the third acute experiment when the 4194 lead tip was positioned under the sternum at the location of the $6^{th}$ rib. FIG. 10 shows the position dependence of the substernal/retrosternal electrode. When the pacing electrode is optimally located over the ventricular surface of the cardiac silhouette (as observed via fluoroscopy), pacing threshold is low. Low thresholds were very repeatable in this anatomical location, even at shorter pulse durations and in many different pacing configurations. Extra-cardiac stimulation generally was not apparent at low thresholds and longer pulse durations throughout this experiment.

All three acute experiments demonstrated the feasibility of pacing from a substernal/retrosternal electrode location. The lowest threshold results across the three acute procedures were 0.8 volts, 7 volts and 0.8 volts, respectively, with the second acute procedure involving an anatomical difference (pericardial adhesions) that tipped the ventricular surface of the heart away from its normal orientation with the sternum, resulting in higher pacing thresholds. However, for the purposes of anti-tachycardia pacing, conventional devices typically default to maximum output (8V at 1.5 ms) for ATP therapy delivery. Given this, even the 7V threshold obtained in the second acute experiment could be satisfactory for ATP therapy.

The ability to capture the heart at low pacing thresholds was dependent upon electrode position. As observed through these experiments, the substernal/retrosternal pacing electrode provides the best outcomes when positioned approximately over the ventricular surface of the cardiac silhouette, which is easily observed via fluoroscopy and encompasses a reasonably large target area for lead placement. In the third acute experiment, for example, capture was achieved at three separate positions, with the lead tip at approximately ribs 4, 5 and 6, all of which were near the ventricular surface of the cardiac silhouette.

Pacing thresholds increased with shorter pulse durations. In many instances, however, low pacing thresholds were obtained even at short pulse widths, especially when the substernal/retrosternal pacing electrode was positioned over the ventricular surface of the cardiac silhouette. In other instances, longer pulse durations (10-20 ms) were necessary to obtain capture or to achieve lower capture thresholds.

Across experiments, it was possible to pace from the substernal/retrosternal lead to an active can emulator positioned near the animal's side (unipolar) and also from the substernal/retrosternal lead to a subcutaneous ICD lead (unipolar). If a subcutaneous ICD system incorporated a lead, placed substernally, for the purpose of anti-tachycardia pacing, both of the aforementioned unipolar pacing configurations would be available for a physician to choose from.

These experiments also demonstrated the ability to pace in a bipolar configuration entirely under the sternum (4194 tip (−) to 4194 ring (+), substernally), indicating that either a bipolar lead positioned under the sternum might be used for anti-tachycardia pacing purposes.

Overall, the results of these acute experiments demonstrate the ability to pace the heart from a substernal/retrosternal location, with the lead not entering the vasculature or the pericardial space, nor making intimate contact with the heart. The low threshold values obtained when pacing from a substernal/retrosternal lead location in these acute experiments suggest that pain-free pacing for the purpose of anti-tachycardia pacing in a subcutaneous ICD system is within reach.

In some instances, the electrodes of the various leadless IPGs described herein may be shaped, oriented, designed or otherwise configured to reduce extra-cardiac stimulation. For example, the electrodes of the various leadless IPGs described herein may be shaped, oriented, designed or otherwise configured to focus, direct or point the electrodes toward heart 26. In this manner, pacing pulses delivered via the electrodes of the various leadless IPGs described herein are directed toward heart 26 and not outward toward skeletal muscle. For example, the electrodes of the various leadless IPGs described herein may be partially coated or masked with a polymer (e.g., polyurethane) or another coating material (e.g., tantalum pentoxide) on one side or in different regions so as to direct the pacing signal toward heart 26 and not outward toward skeletal muscle.

Various examples have been described. These and other examples are within the scope of the following claims.

The invention claimed is:

1. An implantable cardiac pacing system comprising:
   a housing configured to be implanted substantially within an anterior mediastinum of a patient, wherein the anterior mediastinum represents a non-vascular, extra-pericardial location;

one or more anchoring mechanisms positioned along a length of the housing, wherein the one or more anchoring mechanisms are configured to anchor the housing within the anterior mediastinum of the patient such that the housing is physically isolated from a pericardium of the patient, wherein the one or more anchoring mechanisms comprises one or more tines extending from the housing, and wherein the one or more anchoring mechanisms are configured to affix the housing to loose connective tissue or other structures of the anterior mediastinum;

a first electrode on the housing;

a second electrode on the housing; and a pulse generator within the housing and electrically coupled to the first electrode and the second electrode, wherein the pulse generator is configured to deliver pacing pulses to a heart of the patient via a therapy vector formed between the first and second electrodes.

2. The system of claim 1, wherein the pulse generator is configured to provide one of bradycardia pacing, antitachycardia (ATP) pacing, and post-shock pacing to the patient via the lead.

3. The system of claim 1, wherein the housing is configured to be implanted substantially within the anterior mediastinum such that the first and second electrodes are located over one of a cardiac silhouette of a ventricle of the heart as observed via an anterior-posterior (AP) fluoroscopic view of the heart.

4. The system of claim 3, further comprising:
a third electrode on the housing; and
a fourth electrode on the housing,
wherein the housing is configured to be implanted substantially within the anterior mediastinum such that the third and fourth electrodes are located over a cardiac silhouette of an atrium of the heart as observed via the AP fluoroscopic view of the heart.

5. The system of claim 1, further comprising:
a third electrode on the housing; and
a fourth electrode on the housing,
wherein the housing is configured to be implanted substantially within the anterior mediastinum such that the pulse generator provides pacing pulses to a ventricle of the heart via the first and second electrode and provides pacing pulses to an atrium of the heart via the third and fourth electrodes.

6. The system of claim 1, wherein the housing comprises a first housing and the pulse generator comprises a first pulse generator and the one or more anchoring mechanisms comprise one or more first anchoring mechanisms, the system further comprising:
a second housing separate from the first housing;
one or more second anchoring mechanisms positioned along a length of the second housing, wherein the one or more second anchoring mechanisms are configured to anchor the second housing within the anterior mediastinum of the patient such that the second housing is physically isolated from the pericardium of the patient;
a third electrode on the second housing;
a fourth electrode on the second housing; and
a second pulse generator within the second housing,
wherein the first and second housings are configured to be implanted substantially within the anterior mediastinum of the patient such that pacing pulses are delivered to a first chamber of the heart via the first and second electrodes of the first housing and pacing pulses are delivered to a second chamber of the heart via the third and fourth electrodes of the second housing.

7. The system of claim 6, further comprising:
a first communication module within the first housing; and
a second communication module within the second housing,
wherein the first communication module transmits a telemetry communication to the second communication module to coordinate the pacing pulses delivered to the first and second chambers of the heart.

8. The system of claim 1, wherein the housing comprises a first housing and the pulse generator comprises a first pulse generator, and the one or more anchoring mechanisms comprise one or more first anchoring mechanisms, the system further comprising:
a second housing separate from the first housing;
one or more second anchoring mechanisms positioned along a length of the second housing, wherein the one or more second anchoring mechanisms are configured to anchor the second housing within the anterior mediastinum of the patient such that the second housing is physically isolated from the pericardium of the patient;
a third electrode on the second housing;
a fourth electrode on the second housing; and
wherein the first and second housings are configured to be implanted substantially within the anterior mediastinum of the patient such that the first and second electrodes of the first housing sense electrical signals of a first chamber of the heart and the third and fourth electrodes of the second housing sense electrical signals of a second chamber of the heart.

9. The system of claim 8, wherein the one or more second anchoring mechanisms comprise a plurality of anchoring mechanisms.

10. The system of claim 1, wherein the pulse generator is configured to deliver pacing pulses having pulse widths greater than or equal to two (2) milliseconds.

11. The system of claim 1, wherein the pulse generator is configured to deliver pacing pulses having pulse widths between approximately one and a half (1.5) milliseconds and twenty (20) milliseconds.

12. The system of claim 1, wherein the pulse generator is configured to deliver pacing pulses having pulse widths greater than two (2) milliseconds and less than eight (8) milliseconds.

13. The system of claim 1, wherein the pulse generator is configured to deliver pacing pulses having pulse amplitudes between approximately one (1) and twenty (20) volts.

14. The system of claim 1, wherein the pulse generator is configured to deliver pacing pulses having pulse amplitudes less than five (5) volts.

15. The system of claim 1, wherein the pulse generator is configured to deliver pacing pulses having pulse amplitudes between approximately one (1) volt and two and a half (2.5) volts.

16. The system of claim 1, wherein the one or more anchoring mechanisms comprise a plurality of anchoring mechanisms.

17. The system of claim 1, wherein each anchoring mechanism of one or more anchoring mechanisms is configured to anchor the housing within the anterior mediastinum of the patient by anchoring the housing to at least one of loose connective tissue, bone, fascia, or muscle within the anterior mediastinum of the patient.

18. The system of claim 1, wherein the housing includes a first housing portion comprising a conductive material, wherein the housing includes a second housing portion comprising a conductive material, and wherein the system further comprises:
 a spacer that separates the first housing portion and the second housing portion, wherein the spacer comprises a non-conductive material.

19. A method comprising:
 providing a leadless implantable pulse generator (IPG) substantially within an anterior mediastinum of a patient, the leadless IPG including a housing configured to be implanted substantially within the anterior mediastinum, wherein the anterior mediastinum represents a non-vascular, extra-pericardial location, one or more anchoring mechanisms positioned along a length of the housing, wherein the one or more anchoring mechanisms are configured to anchor the housing within the anterior mediastinum of the patient such that the housing is physically isolated from a pericardium of the patient, wherein the one or more anchoring mechanisms comprises one or more tines extending from the housing, and wherein the one or more anchoring mechanisms are configured to affix the housing to loose connective tissue or other structures of the anterior mediastinum, a first electrode on the housing, a second electrode on the housing, and a pulse generator within the housing and electrically coupled to the first electrode and the second electrode;
 generating one or more stimulation pulses with the implantable pulse generator; and
 delivering the one or more stimulation pulses to a heart of the patient via the first and second electrode of the leadless IPG implanted substantially within the anterior mediastinum.

20. The method of claim 19, wherein delivering the one or more stimulation pulses comprises delivering one or more bradycardia pacing pulses, antitachycardia (ATP) pulses, and post-shock pacing pulses.

21. The method of claim 19, wherein the leadless IPG further includes a third electrode on the housing and a fourth electrode on the housing and delivering the one or more stimulation pulses comprises delivering stimulation pulses to a ventricle of the heart via the first and second electrodes on the housing and delivering one or more stimulation pulses to an atrium of the heart via the third and fourth electrodes on the housing.

22. The method of claim 21, wherein the housing of the leadless IPG is configured to be implanted substantially within the anterior mediastinum such that the first and second electrodes are located over a cardiac silhouette of a ventricle of the heart as observed via an anterior-posterior (AP) fluoroscopic view of the heart and the third and fourth electrodes are located over a cardiac silhouette of an atrium of the heart as observed via the AP fluoroscopic view of the heart.

23. The method of claim 19, wherein the leadless IPG comprises a first leadless IPG and the one or more anchoring mechanisms comprise one or more first anchoring mechanisms, the method further comprising:
 providing a second leadless implantable pulse generator (IPG) substantially within the anterior mediastinum of the patient, the second leadless IPG including a second housing configured to be implanted substantially within the anterior mediastinum, one or more second anchoring mechanisms positioned along a length of the second housing, wherein the one or more second anchoring mechanisms are configured to anchor the second housing within the anterior mediastinum of the patient such that the second housing is physically isolated from the pericardium of the patient, a third electrode on the second housing, a fourth electrode on the second housing, and a second pulse generator within the second housing and electrically coupled to the third electrode and the fourth electrode;
 generating one or more stimulation pulses with the second implantable pulse generator; and
 delivering the one or more stimulation pulses, via the third and fourth electrode of the second leadless IPG, to a different chamber of the heart than the stimulation pulses delivered by the first leadless IPG.

24. The method of claim 23, further comprising transmitting a communication from the first leadless IPG to the second leadless IPG to coordinate the stimulation pulses delivered to the different chambers of the heart.

25. The method of claim 19, wherein generating and delivering the one or more stimulation pulses comprises generating and delivering one or more stimulation pulses having pulse widths between approximately one and a half (1.5) milliseconds and twenty (20) milliseconds.

* * * * *